US011008562B2

(12) United States Patent
Birikh et al.

(10) Patent No.: US 11,008,562 B2
(45) Date of Patent: *May 18, 2021

(54) CALCIUM INDEPENDENT PECTINASES WITH IMPROVED THERMOSTABILITY

(71) Applicant: Metgen OY, Kaarina (FI)

(72) Inventors: Klara Birikh, Kaarina (FI); Anu Minna Maaret Suonpaa, Kaarina (FI)

(73) Assignee: Metgen OY, Kaarina (FI)

( * ) Notice: Subject to any disclaimer, the term of this patent is extended or adjusted under 35 U.S.C. 154(b) by 211 days.

This patent is subject to a terminal disclaimer.

(21) Appl. No.: 16/062,586

(22) PCT Filed: Dec. 8, 2016

(86) PCT No.: PCT/EP2016/080261
§ 371 (c)(1),
(2) Date: Sep. 27, 2018

(87) PCT Pub. No.: WO2017/102543
PCT Pub. Date: Jun. 22, 2017

(65) Prior Publication Data
US 2020/0149027 A1     May 14, 2020

(30) Foreign Application Priority Data

Dec. 15, 2015   (EP) .................................. 15200249

(51) Int. Cl.
| *C12N 9/88* | (2006.01) |
| *C12N 1/20* | (2006.01) |
| *C12N 15/00* | (2006.01) |
| *C12N 15/10* | (2006.01) |
| *C12N 15/70* | (2006.01) |

(52) U.S. Cl.
CPC ............ *C12N 9/88* (2013.01); *C12N 15/102* (2013.01); *C12N 15/70* (2013.01); *C12Y 402/02002* (2013.01)

(58) Field of Classification Search
CPC ...................................................... C12N 9/88
See application file for complete search history.

(56) References Cited

U.S. PATENT DOCUMENTS 10,246,696 B2 *  4/2019  Birikh ............ C12Y 402/02002

FOREIGN PATENT DOCUMENTS

WO      2008138109      11/2008

OTHER PUBLICATIONS

Studer. Residue mutations and their impact on protein structure and function: detecting beneficial and pathogenic changes. Biochem. J. (2013) 449, 581-594.*
PCT International Search Report and Written Opinion for International Application No. PCT/EP2016/080261, dated Feb. 20, 2017, 12 pgs.
Database UniProt [Online], "SubName: Full=Ptate lyase {ECO:0000313|EMBL:KIL52125.1}; EC=4.2.2.2 {ECO:0000313|EMBL:KIL52125.1};" retrieved from EBI accession No. UNIPROT:A0A0C2RPE1, Apr. 1, 2015, 2 pgs.
International Search Report and Written Opinion for International Application No. PCT/EP2016/080265, dated Feb. 15, 2017, 12 pgs.
Liang et al., Improving the Thermoactivity and Thermostability of Pectate Lyase from Bacillus Pumilus for Ramie Degumming, Appl Microbiol Biotechnol, Jul. 12, 2014, pp. 2673-2682.
Nakaniwa et al., An in vitro Evaluation of a Thermostable Pectate Lyase by Using Error-Prone PCR, Journal of Molecular Catalysis, Jul. 31, 2003, pp. 127-131.
Xiao et al., Improvement of the Thermostability and Activity of a Pectate Lyase by Single Amino Acid Substitutions, Using a Strategy Based on Melting-Temperature-guided Sequence Alignment, Applied and Environmental Microbiology, Feb. 2008, pp. 1183-1189, vol. 74 No. 4.

* cited by examiner

*Primary Examiner* — Yong D Pak
(74) *Attorney, Agent, or Firm* — Patent Law Works, LLP

(57) ABSTRACT

The invention is in the field of protein chemistry, in particular in the field of enzymology. It provides pectinases, i.e. polypeptides with pectin-degrading properties. In particular the invention provides polypeptides with pectate lyase activity (EC 4.2.2.2). Enzymes according to the invention have improved properties, such as improved thermostability and decreased calcium dependence.

Figure 1:
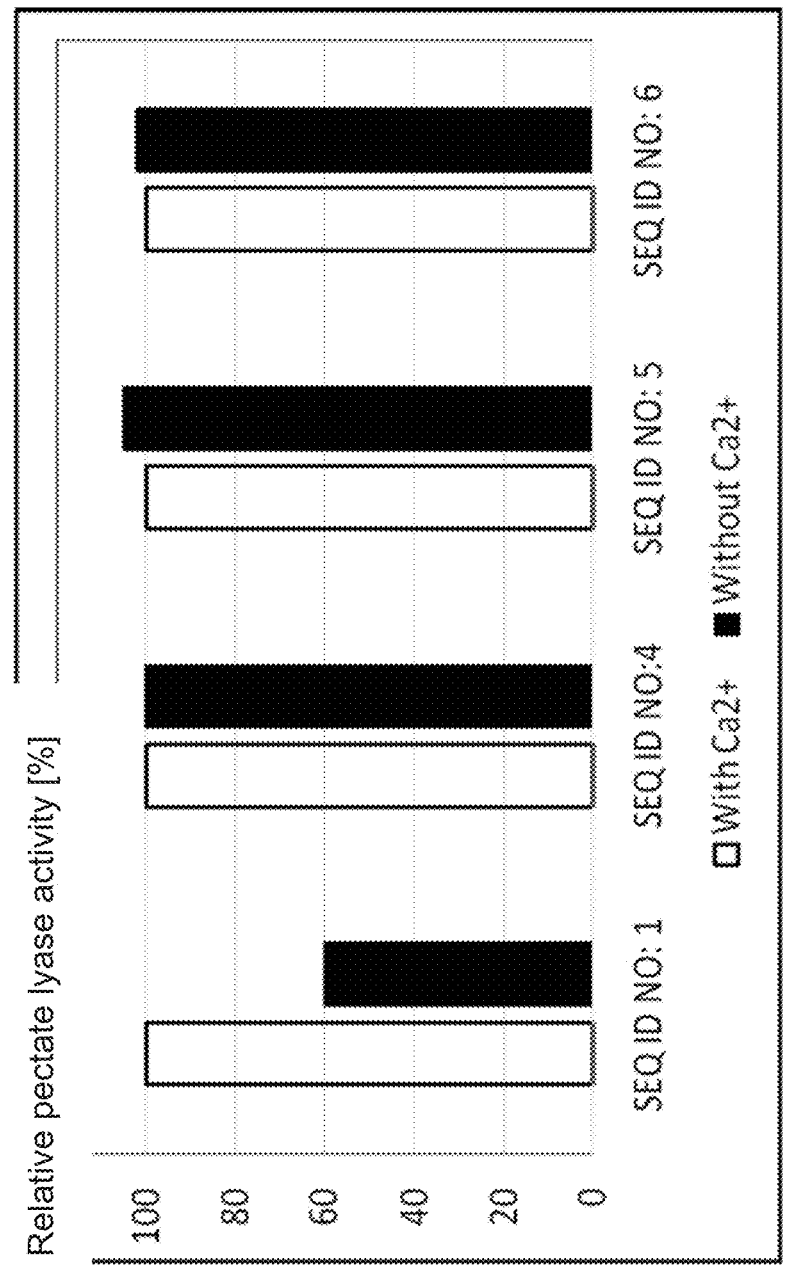

21 Claims, 2 Drawing Sheets
Specification includes a Sequence Listing.

CALCIUM INDEPENDENT PECTINASES WITH IMPROVED THERMOSTABILITY

FIELD OF THE INVENTION

The invention is in the field of protein chemistry, in particular in the field of enzymology. It provides pectinases, i.e. polypeptides with pectin-degrading properties. In particular the invention provides polypeptides with pectate lyase activity (EC 4.2.2.2). Enzymes according to the invention have improved properties, such as improved thermostability and decreased calcium dependence.

BACKGROUND OF THE INVENTION

Plant cell wall degrading enzymes are carbohydrate-active enzymes that have been classified in different families based on homology criteria [http://www.cazy.org/, Cantarel et al., 2009, Nucleic Acids Res 37: D233-D238].

Pectate lyases (EC 4.2.2.2), are an important group of plant cell wall degrading enzymes. They cleave pectin using an eliminative cleavage of (1->4)-alpha-D-galacturonan yielding oligosaccharides with 4-deoxy-alpha-D-galact-4-enuronosyl groups at their non-reducing ends. They are mainly produced by plant pathogens and plant-associated organisms, and only rarely by animals. Pectate lyases are also commonly produced in bacteria, either by bacteria living in close proximity with plants or by gut bacteria that find plant material in the digestive tract of their hosts. [Hugouvieux-Cotte-Pattat et al., Environmental Microbiology reports (2014) doi 10, 1111/1758-2229, 12166].

Pectate lyases favor pectate, the anion, over pectin, the methylated ester, which is the preferred substrate of pectin lyase EC 4.2.2.10. Pectate lyases are also known under different names, such as alpha-1,4-D-endopolygalacturonic acid lyase, endo-alpha-1,4-polygalacturonic acid lyase, endogalacturonate transeliminase, endopectin methyltranseliminase, pectate transeliminase, pectic acid lyase, pectic acid transeliminase, pectic lyase, pectin trans-eliminase, PGA lyase, polygalacturonate lyase, polygalacturonic acid lyase, polygalacturonic acid trans-eliminase, polygalacturonic transeliminase and PPase-N.

When pectate lyases are used in industrial processes, it is often advantageous that they are stable at higher temperatures (thermostable) and resistant to alkaline conditions. Thermostable alkaline pectate lyases for instance have potential applications in the textile industry as an alternative to chemical-based ramie degumming processes. Such enzymes have been described, and have been isolated and characterized from bacterial sources, mainly *Bacillus* [Swarupa Rani Chiliveri et al., Carbohydrate Polymers (2014), 111: 264-272, Zhou et al., Appl Environ Microbiol (2015) 81: 5714-5723].

Cleavage by pectate lyases requires the presence of cations, such as manganese, nickel, iron, cobalt or calcium ions [Celia Marin-Rodriguez et al., J. Exp. Bot. (2002) 53: 2115-2119, Hugouvieux-Cotte-Pattat et al., Environmental Microbiology reports (2014) doi 10, 1111/1758-2229, 12166], with only rare exceptions [Kazemi-Pour et al., Proteomics (2004) 10: 3177-3186].

Recently, another calcium-dependent thermostable pectate lyase was isolated from *Bacillus*, cloned, sequenced and characterized [Takao et al, Biosci. Biotechnol. Biochem. (2000) 64: 2360-2367, Takao et al., Biosci. Biotechnol. Biochem. (2001) 65: 322-329].

Although these enzymes are useful in a wide variety of industrial processes, they may be less suited for multi-enzyme processes, because of their calcium-dependence, since calcium ions may interfere with the working mechanism of other enzymes. Most notably, in a process wherein biomass is degraded to glucose by a variety of hydrolytic enzymes including pectate lyase, the calcium ions would have to be removed completely before the glucose could be converted to fructose by glucose isomerase, since this latter enzyme is inhibited by calcium [Food Biotechnology, Second Edition, Food Science and Technology, Ed. Anthony Pometto, Kalidas Shetty, Gopinadhan Paliyath, Robert E. Levin, ISBN 1420027972, 9781420027976].

Moreover, calcium ions may form insoluble salts with various anions, which can cause problems with industrial processes, such as ultra-filtration and build up on hardware.

Hence, there is a need in the art for improved polypeptides with pectate lyase activity.

SUMMARY OF THE INVENTION

The present invention addresses this need in that it provides a calcium-independent pectate lyase. More in particular, the invention provides a polypeptide with pectate lyase activity comprising an amino acid sequence that is at least 70% identical to the amino acid according to SEQ ID NO: 1, wherein the polypeptide comprises a leucine residue at an amino acid position corresponding to position 231 in SEQ ID NO: 1.

The invention also relates to a composition comprising a polypeptide as described above, a nucleic acid encoding a polypeptide as described above, a vector comprising such a nucleic acid and a composition comprising such a nucleic acid or a vector.

The invention also provides a recombinant host cell comprising a nucleic acid, a vector or a composition as described above.

Moreover, the invention relates to a method for producing a polypeptide as described above, comprising the steps of: culturing a recombinant host cell as described above, under conditions suitable for the production of the polypeptide, and recovering the polypeptide obtained, and optionally purifying the polypeptide.

In addition, the invention relates to a polypeptide as described above in an application selected from the group consisting of pulp delignification, degrading or decreasing the structural integrity of lignocellulosic material, textile dye bleaching, wastewater detoxifixation, xenobiotic detoxification, production of a sugar from a lignocellulosic material and recovering cellulose from a biomass.

The invention also relates to a method for improving the thermostability of a polypeptide with pectate lyase activity comprising an amino acid sequence that is at least 70% identical to the amino acid according to SEQ ID NO: 1, the method comprising the step of altering the amino acid at a position corresponding to position 231 in SEQ ID NO: 1 to a leucine residue.

The invention also relates to a method for decreasing, abolishing or removing the calcium dependence of a polypeptide with pectate lyase activity comprising an amino acid sequence that is at least 70% identical to the amino acid according to SEQ ID NO: 1, the method comprising the step of altering the amino acid at a position corresponding to position 231 in SEQ ID NO: 1 to a leucine residue.

LEGEND TO THE FIGURES

FIG. 1: Diagram showing the relative pectate lyase activity of polypeptides according to SEQ ID NO: 1, SEQ ID NO:

4, SEQ ID NO: 5 and SEQ ID NO: 6. Pectate lyase activity was determined in the presence and absence of calcium ions according to the method described in example 7. Whereas the wild type sequence according to SEQ ID NO: 1 was calcium dependent, the mutated polypeptides carrying the A231L mutation (SEQ ID NO:s 4-6) were calcium independent.

Figure 2:
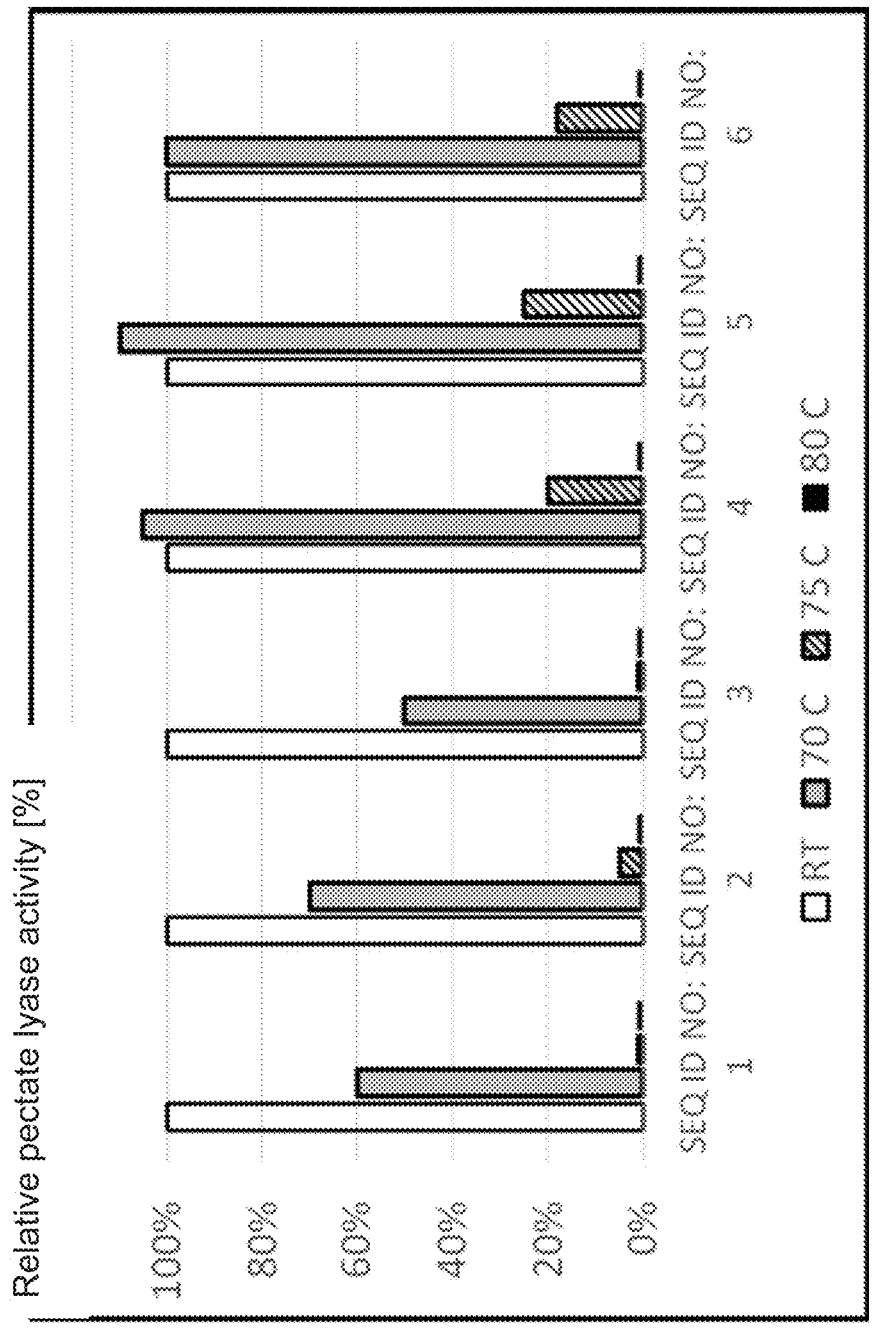

FIG. 2: Thermostability of polypeptides according to SEQ ID NO: 1-6. Diagram showing the relative pectate lyase activity of the polypeptides without the A231L mutation (SEQ ID NO: 1, 2 and 3) and the relative pectate lyase activity of polypeptides with the A231L mutation (SEQ ID NO:s 4, 5 and 6) after a pre-incubation of 10 minutes at elevated temperatures. RT=Room Temperature, 70 C is 70 degrees Celsius.

DETAILED DESCRIPTION OF THE INVENTION

The present invention is based on our observation that a single amino acid substitution at a position corresponding to the amino acid position 231 in SEQ ID NO: 1 (A231L variant) in different pectate lyases decreases or abolishes the calcium dependence of the enzyme. We also found that the A231L variant remained its pectate lyase activity.

As used herein, the term "A231L variant" indicates that the amino acid corresponding to the alanine residue at position 231 of SEQ ID NO: 1 is replaced by a leucine residue.

The term "amino acid substitution" is used herein in the same way as it is commonly used, i.e. the term refers to a replacement of one or more amino acids in a protein with one or more other amino acids. Such an amino acid substitution may also be referred to as a mutation, a variant or a variation.

We observed the same phenomenon in pectate lyases that were homologous to the polypeptide with an amino acid sequence according to SEQ ID NO: 1. When an A231L amino acid variation was introduced in polypeptides that were 93% and 89% identical to the polypeptide according to SEQ ID NO: 1, this also decreased or abolished the calcium dependence of both these enzymes.

The invention thus relates to a polypeptide with pectate lyase activity comprising an amino acid sequence that is at least 70% identical to the amino acid according to SEQ ID NO: 1, wherein the polypeptide comprises a leucine residue at an amino acid position corresponding to position 231 in SEQ ID NO: 1. This is herein referred to as an A231L variant of SEQ ID NO: 1.

Polypeptides with pectate lyase activity are also referred herein as pectate lyases, or pectate lyase enzymes.

The term "pectate lyase activity" is used herein to indicate the ability of a polypeptide to cleave pectin using an eliminative cleavage of (1->4)-alpha-D-galacturonan yielding oligosaccharides with 4-deoxy-alpha-D-galact-4-enuronosyl groups at their non-reducing ends. Methods of measuring this activity are well known in the art.

The term "at least 70%" is used herein to include at least 71%, 72%, 73%, 74%, 75%, 76%, 77%, 78%, 79%, 80%, 81%, 82%, 83%, 84%, 85%, 88%, 87%, 88%, 89%, 90% or more, such as 91%, 92%, 93%, 94%, 95%, 99%, 97%, 98%, 99%, or even 100%.

As used herein, the degree of identity between two or more amino acid sequences is equivalent to a function of the number of identical positions shared by the sequences; i.e., % identity=number of identical positions divided by the total number of aligned positions×100, excluding gaps, which need to be introduced for optimal alignment of the two sequences, and overhangs. The alignment of two sequences is to be performed over the full length of the polypeptides.

The comparison (aligning) of sequences is a routine task for the skilled person and can be accomplished using standard methods known in the art. For example, a freeware conventionally used for this purpose is "Align" tool at NCBI recourse http://blast.ncbi.nlm.nih.gov/Blast.cgi?PAGE_TYPE=BlastSearch&BLAST_SPEC=blast2 seq&LINK_LOC=align2seq, Other commercial and open software such as Vector NTI are also suitable for this purpose, Introduction of a specific mutation in a recombinant gene is also among the routine skills of a molecular biologist. Specific guidance may be obtained from Methods in Molecular Biology Vol 182, "In vitro mutagenesis protocols", Eds Jeff Braman, Humana Press 2002. There are commercially available kits for performing site-directed mutagenesis (for example, QuikChange II XL Site-Directed Mutagenesis kit Agilent Technologies cat No 200521).

SEQ ID NO: 1 provides the amino acid sequence of a known polypeptide [Takao et al, Biosci. Biotechnol. Biochem. (2000) 64: 2360-2367, Takao et al., Biosci. Biotechnol. Biochem. (2001) 65: 322-329] with pectate lyase activity. We replaced the alanine residue at position 231 of SEQ ID NO: 1 with a leucine residue, thereby obtaining a polypeptide according to SEQ ID NO: 4. We found that the calcium dependence of the pectate lyase activity was thereby decreased, diminished or abolished. This is further referred to herein as "calcium independence".

The "calcium independence" of an enzyme can be measured according to the procedures as disclosed in examples 5 and 7. Therein the activity of the pectate lyase is measured in the presence and absence of CaCl2.

A pectate lyase is considered to be calcium independent if the activity of the enzyme in the absence of CaCl2 is not decreased by more than 20% as compared to its activity in the presence of 0.5 mM CaCl2, under the conditions exemplified in example 5. In a preferred embodiment, the activity of the enzyme is not decreased in the absence of CaCl2. The enzyme is considered to be calcium dependent if it is not calcium independent. We also found that the amino acid position corresponding to position 231 in SEQ ID NO: 1 could be changed in polypeptides with an amino acid sequence homologous to the sequence according to SEQ ID NO: 1 with the same effect. We constructed two pectate lyases that were 93% (SEQ ID NO: 2) and 89% (SEQ ID NO: 3) identical with the amino acid sequence according to SEQ ID NO: 1. These homologous peptides were also found to be calcium dependent in that their pectate lyase activity decreased to only 60% when calcium was omitted from the reaction buffer (FIG. 1).

We observed that these two homologous pectate lyases became calcium-independent when the amino acid corresponding to position 231 in SEQ ID NO: 1 was changed to a leucine residue in order to obtain polypeptides comprising an amino acid sequences according to SEQ ID NO:s 5 and 6 respectively.

The wild type sequence and the homologous polypeptides according to SEQ ID NO: 2 and SEQ ID NO: 3 only displayed 60% of their activity in the absence of calcium, i.e. when calcium was omitted from the activity assay. However, the polypeptide according to SEQ ID NO: 4 and its homologous polypeptides according to SEQ ID NO: 5 and SEQ ID NO: 6 (all three carrying the A231L mutation) showed full pectate lyase activity in the absence of calcium (100, 105 and 102% respectively, FIG. 1). It is concluded that the pectate lyase activity of the wild type depends on calcium, whereas the activity of the A231L variants is not dependent on calcium.

The expression "the amino acid corresponding to position 231 in SEQ ID NO: 1" is to be understood as follows. If such a position is to be determined in a given amino acid sequence that is at least 70% identical with the amino acid sequence according to SEQ ID NO: 1, then the two sequences are first to be aligned. That may be done by routine methods and software available in the art. The amino acid in the given amino acid sequence corresponding to amino acid 231 in SEQ ID NO: 1 is then the amino acid aligning with the alanine residue at position 231 in SEQ ID NO: 1.

We performed a homology search for proteins homologous to SEQ ID NO: 1 using SEQ ID NO: 1 as the query sequence in the "Standard protein BLAST" software, available at http://blast.ncbi.nlm.nih.gov/Blast.cgi?PROGRAM=blastp&PAGE_TYPE=BlastSearch&LI NK_LOC=blasthome. More information on the software and database versions is available at the National Center for Biotechnology Information at National library of Medicine at National institute of Health internet site www.ncbi.nlm.nih.gov. Therein, a number of molecular biology tools including BLAST (Basic Logical Alignment Search Tool) is to be found. BLAST makes use of the following databases: All non-redundant GenBank CDS translations+PDB+SwissProt+PIR+PRF excluding environmental samples from WGS projects.

There were no polypeptides found comprising an amino acid sequence that is at least 70% identical to the amino acid according to SEQ ID NO: 1.

The term "amino acid variant", "variant", "mutant" or "sequence variant" or equivalent has a meaning well recognized in the art and is accordingly used herein to indicate an amino acid sequence that has at least one amino acid difference as compared to another amino acid sequence, such as the amino acid sequence from which it was derived.

Surprisingly, we also found that the A231L mutation caused the polypeptides to have an improved thermostability.

The term "mutant protein" or "mutation" is also used herein to refer to a polypeptide with pectate lyase activity as described herein, comprising a leucine residue at an amino acid position corresponding to position 231 in SEQ ID NO: 1.

The term "wild type protein" is also used herein to indicate a polypeptide identical to the mutant protein, with the exception that it does not comprise a leucine residue at an amino acid position corresponding to position 231 in SEQ ID NO: 1.

The term "improved thermostability" in reference to a mutant polypeptide, as used herein, means that the mutant polypeptide has a higher residual pectate lyase activity than the corresponding wild type protein, after incubation for 10 minutes in 50 mM Tris-HCl pH 8.0 at a suitable temperature.

The term "suitable temperature" as used in this context refers to a temperature at which the wild type protein loses part of its pectate lyase activity after 10 minutes of incubation in 50 mM Tris-HCl pH 8.0. In other words, the term "suitable temperature" refers to a temperature chosen from a temperature range between temperatures X and Y, wherein X is the lowest temperature at which a wild type polypeptide shows a detectable loss of activity after 10 minutes of incubation in 50 mM Tris-HCl pH 8.0 and wherein temperature Y is the lowest temperature at which a wild type polypeptide loses all activity after 10 minutes of incubation in 50 mM Tris-HCl pH 8.0.

In a more concrete example, the term "improved thermostability" is exemplified in that the A231L variant polypeptide according to SEQ ID NO: 4 exhibited more pectate lysase activity after pre-incubation at elevated temperatures than the wild type polypeptide (SEQ ID NO: 1). The same was found for the homologous polypeptide according to SEQ ID NO: 5 as compared to the same polypeptide without the A231L variant (SEQ ID NO: 2). Also, the A231L variant polypeptide according to SEQ ID NO: 6 was more thermostable than its non-variant counterpart according to SEQ ID NO: 3.

In more detail, we measured the residual relative pectate lyase activity after heat treatment of polypeptides comprising an amino acid sequence according to SEQ ID NO: 4, SEQ ID NO: 5 and SEQ ID NO: 6 and compared this activity to that of a pre-treated polypeptide with an amino acid sequence of SEQ ID NO: 1, 2 and 3 respectively. More specifically, the polypeptides were heated to 70, 75 or 80 degrees Celsius for 10 minutes in 50 mM Tris-HCl at pH 8.0. The residual activity was measured at 60 degrees Celsius at pH 8.0 as described in example 5 and compared to the residual activity of the same polypeptides after pre-incubation at room temperature for 10 minutes. The results are shown in table 1.

TABLE 1

Relative pectate lyase activity after pre-incubation at elevated temperatures.

| Temp. | SEQ ID NO: 1 | SEQ ID NO: 2 | SEQ ID NO: 3 | SEQ ID NO: 4 | SEQ ID NO: 5 | SEQ ID NO: 6 |
|---|---|---|---|---|---|---|
| RT | 100% | 100% | 100% | 100% | 100% | 100% |
| 70 C. | 60% | 70% | 50% | 105% | 110% | 100% |
| 75 C. | 1% | 5% | 1% | 20% | 25% | 18% |
| 80 C. | 1% | 1% | 1% | 1% | 1% | 1% |

We observed that the pectate lyase activity of the wildtype polypeptide according to SEQ ID NO: 1 decreased to 60% after pre-incubation at 70 degrees Celsius for 10 minutes. The same was found for the homologous polypeptides with an amino acid sequence according to SEQ ID NO: 2 and 3 (70 and 50% respectively) In contrast, the activity of the A231L variants according to SEQ ID NO: 4, SEQ ID NO: 5 and SEQ ID NO: 6 were unaffected, or even higher than the same polypeptides pre-incubated at room temperature.

We also observed that, in contrast to the wild type sequence (SEQ ID NO: 1) and its homologues according to SEQ ID NO: 2 and SEQ ID NO: 3, the A231L variant polypeptides (SEQ ID NO:s 4-6) all showed considerable pectate lyase activity after pre-incubation at 75 degrees C., whereas the wild type enzyme according to SEQ ID NO: 1 and its homologues according to SEQ ID NO: 2 and SEQ ID NO: 3 did not show any significant activity under these conditions (5% or less).

The wild-type enzyme according to SEQ ID NO: 1, nor its homologues according to SEQ ID NO: 2 and SEQ ID NO: 3, nor the variants survived pre-treatment at 80 degrees Celsius for 10 minutes. This is graphically represented in FIG. 2.

Thermostable pectate lyases have been described to be produced by bacteria of the genus *Bacillus* [Takao et al, Biosci. Biotechnol. Biochem. (2000) 64: 2360-2367, Takao et al., Biosci. Biotechnol. Biochem. (2001) 65: 322-329, Swarupa Rani Chiliveri et al., Carbohydrate Polymers (2014), 111: 264-272, Zhou et al., Appl Environ Microbiol (2015) 81: 5714-5723], hence in a preferred embodiment the invention relates to a polypeptide as described herein wherein the polypeptide is capable of being expressed in a *Bacillus* species, more preferably *Bacillus subtilis*.

We have shown that several polypeptides may be produced that are homologous to the wild-type sequence according to SEQ ID NO: 1 and still retain their pectate lyase activity. A BLAST search revealed that pectate lyases are available from bacterial origin, in particular from *Bacillus* species, with an identity as low as 52% or less as compared to SEQ ID NO: 1. The skilled person will therefore have no difficulty in constructing a polypeptide with pectate lyase activity that is at least 70% identical to the sequence of SEQ ID NO: 1 following the procedures and guidance provided herein. He will also be able to make the A231L variants as described herein, thereby obtaining a calcium-independent pectate lyase with an improved thermostability.

In a preferred embodiment, the invention relates to a polypeptide as described herein comprising an amino acid sequence that is at least 75% identical to the amino acid according to SEQ ID NO: 1, such as 80%, 85%. 89%, 90%, 91%, 92%, 93%, 94%, 95%, 96%. 97%, 98%, 99% or even 100%.

Recovery of a polypeptide according to the invention as produced by a host cell may be performed by any technique known to those skilled in the art. Possible techniques include, but are not limited to secretion of the protein into the expression medium, and purification of the protein from cellular biomass. The production method may further comprise a step of purifying the polypeptide obtained. For thermostable polypeptides, non-limiting examples of such methods include heating of the disintegrated cells and removing coagulated thermo labile proteins from the solution. For secreted proteins, non-limiting examples of such methods include ion exchange chromatography, and ultra-filtration of the expression medium. It is preferred that the purification method of choice is such that the purified protein retains its activity.

Accordingly, in a further preferred embodiment, the invention relates to a polypeptide as described herein wherein the polypeptide is an isolated polypeptide.

We have shown herein that the A231L variants as described are calcium-independent and have an improved thermostability.

The polypeptides as described herein may be used in compositions containing several additional components, such as stabilizers, fillers, cell debris, culture medium etcetera. Hence, the invention provides a composition comprising a polypeptide as described herein.

Polypeptides as described herein may be obtained by expressing a recombinant DNA in a heterologous expression system. The term "heterologous expression system" or equivalent means a system for expressing a DNA sequence from one host organism in a recipient organism from a different species or genus than the host organism. The most prevalent recipients, known as heterologous expression systems, are chosen usually because they are easy to transfer DNA into or because they allow for a simpler assessment of the protein's function. Heterologous expression systems are also preferably used because they allow the upscaling of the production of a protein encoded by the DNA sequence in an industrial process. Preferred recipient organisms for use as heterologous expression systems include bacterial, fungal and yeast organisms, such as for example *Escherichia coli, Bacillus, Corynebacterium, Pseudomonas, Pichia pastoris, Saccharomyces cerevisiae, Yarrowia lipolytica*, filamentus fungi and many more systems well known in the art.

The presently disclosed polypeptides or proteins may be fused to additional sequences, by attaching or inserting, including, but not limited to, affinity tags, facilitating protein purification (S-tag, maltose binding domain, chitin binding domain), domains or sequences assisting folding (such as thioredoxin domain, SUMO protein), sequences affecting protein localization (periplasmic localization signals etc), proteins bearing additional function, such as green fluorescent protein (GFP), or sequences representing another enzymatic activity. Other suitable fusion partners for the presently disclosed polypeptides are known to those skilled in the art.

The present invention also relates to polynucleotides encoding any of the pectate lyase variants disclosed herein. Means and methods for cloning and isolating such polynucleotides are well known in the art.

Furthermore, the present invention relates to a vector comprising a polynucleotide according to the invention, optionally operably linked to one or more control sequences. Suitable control sequences are readily available in the art and include, but are not limited to, promoter, leader, polyadenylation, and signal sequences.

Pectate lyase variants according to various embodiments of the present invention may be obtained by standard recombinant methods known in the art. Briefly, such a method may comprise the steps of: culturing a recombinant host cell as described above under conditions suitable for the production of the polypeptide, and recovering the polypeptide obtained. The polypeptide may then optionally be further purified.

A large number of vector-host systems known in the art may be used for recombinant production of the pectate lyases as described herein. Possible vectors include, but are not limited to, plasmids or modified viruses which are maintained in the host cell as autonomous DNA molecule or integrated in genomic DNA. The vector system must be compatible with the host cell used as is well known in the art. Non-limiting examples of suitable host cells include bacteria (e.g. *E. coli*, bacilli), yeast (e.g. *Pichia Pastoris, Saccharomyces Cerevisae*), fungi (e.g. filamentous fungi) insect cells (e.g. Sf9).

In yet other terms, the invention relates to a method for improving the thermostability of a polypeptide with pectate lyase activity comprising an amino acid sequence that is at least 70% identical to the amino acid according to SEQ ID NO: 1, the method comprising the step of altering the amino acid at a position corresponding to position 231 in SEQ ID NO: 1 to a leucine residue.

In a further preferred embodiment, the invention relates to a method for decreasing, abolishing or removing the calcium dependence of a polypeptide with pectate lyase activity comprising an amino acid sequence that is at least 70% identical to the amino acid according to SEQ ID NO: 1, the method comprising the step of altering the amino acid at a position corresponding to position 231 in SEQ ID NO: 1 to a leucine residue.

The polypeptides with pectate lyase activity according to the present invention may be used in a wide range of different industrial processes and applications, such as cellulose recovery from lignocellulosic biomass, decreasing the energy required for the refining of wood and production of a sugar from a lignocellulosic material. They may also be used in wood pulp preparation, in pulp delignification, textile dye bleaching, wastewater detoxifixation, xenobiotic detoxification, degrading or decreasing the structural integrity of lignocellulosic material and detergent manufacturing.

EXAMPLES

Example 1: Preparation of a Polypeptide According to SEQ ID NO: 1

The DNA construct disclosed in Takao et al., Biosci. Biotechnol. Biochem. (2001) 65: 322-329 encoding the polypeptide according to SEQ ID NO: 1 was optimized for expression in *E. coli* and commercially synthesized and cloned into a standard plasmid vector pET28a+ under the control of T7-RNA-polymerase promoter for expression in *Escherichia coli* BL21(DE3). The nucleotide sequence of the construct is provided herein as SEQ ID NO: 7

Example 2: Preparation of Variants of a Polypeptide According to SEQ ID NO: 1 with Pectate Lyase Activity Homologous protein sequences (according to SEQ ID NO: 2 and SEQ ID NO: 3) were generated by random mutagenesis of SEQ ID NO:s 7 and SEQ ID NO: 8 using error-prone PCR essentially as described (Curr Protoc Mol Biol. 2001 May; Chapter 8: Unit 8.3. doi: 10.1002/0471142727.mb0803s51, Random mutagenesis by PCR. Wilson DS1, Keefe AD) using a commercial random PCR mutagenesis kit (QuikChange® II XL Site-Directed Mutagenesis kit by Agilent Technologies). More in particular, the DNA sequence of SEQ ID NO: 8 was obtained from SEQ ID NO: 7 encoding the polypeptide according to SEQ ID NO: 1. The DNA sequence of SEQ ID NO: 9 was obtained by random mutagenesis of SEQ ID NO: 8 encoding the polypeptide according to SEQ ID NO: 2. SEQ ID NO: 9 is the DNA sequence encoding the polypeptide according to SEQ ID NO: 3.

PCR fragments resulting from error-prone PCR were cloned to the plasmid vector pET28a+ under the control of T7-RNA-polymerase promoter for expression in *Escherichia coli* BL21(DE3), and screened for pectate lyase activity of the recombinant proteins.

Active clones were subjected to further rounds of randomization using the same protocol. The polypeptide according to SEQ ID NO: 2 exhibited pectate lyase activity and was found to be 93% identical with SEQ ID NO: 1. The polypeptide according to SEQ ID NO: 3 also exhibited pectate lyase activity and was found to be 89% identical with SEQ ID NO: 1.

Example 3: Preparation of A231L Variant Polypeptides According to SEQ ID NO: 4-6

In order to prepare a polypeptide according to SEQ ID NO: 4, a mutation was introduced into the polypeptide according to SEQ ID NO: 1 at position 231. The alanine residue from that position in SEQ ID NO: 1 was replaced by a leucine residue. This alteration is herein referred as A231L.

This was achieved by standard site-directed mutagenesis essentially as described in WO 2013/038062. In more detail: To introduce mutation A231L into the gene encoding SEQ ID NO: 1, we carried out two separate PCR reactions:

```
(1) with primers Primer 1
                                        (SEQ ID NO: 13)
gaaattaatacgactcactatagg
and Primer 2 (A231L)
                                        (SEQ ID NO: 14)
GCCATCATGCTGCTGAAACGGACGACCAAAATAGGTG, (2) with Primer3 (A231L)
                                        (SEQ ID NO: 15)
GGTCGTCCGTTTCAGCAGCATGATGGCctgCTGGATATC
and Primer 4
                                        (SEQ ID NO: 16)
ggttatgctagttattgctcagcggtg.
```

In both reactions, recombinant gene without the mutation was used as the template. Primers 1 and 4 bind inside the vector sequence and are not specific to the recombinant gene. Primers 2 and 3 bind inside the recombinant gene and their binding sites overlap. Primer 3 binding site contains the mutation site. Primer 3 represents the mutated (desired) sequence, which is not 100% matching the template (lower case type font in the primer sequence indicates the mismatched nucleotides). However, the primer has enough affinity and specificity to the binding site to produce the desired PCR product. Purified PCR products from reactions (1) and (2) were combined and used as template for PCR reaction with Primer 1 and Primer 4. The product of this reaction, containing the variant sequence of the gene encoding the polypeptide according to SEQ ID NO: 4, was cloned in a plasmid vector for expression in *E. coli*.

The same protocol and the same primers were used for introducing the A231L mutation into the genes encoding the polypeptide according to SEQ ID NO: 2 and SEQ ID NO: 3, thereby yielding polypeptides according to SEQ ID NO: 5 and SEQ ID NO: 6 respectively.

Example 4: Heterologous Expression of Polypeptides with Pectate Lyase Activity For recombinant expression in *E. coli*, recombinant genes were cloned into pET-28 commercial expression vector under the control of T7 bacteriophage promoter.

Protein production was carried out in *E. coli* BL21(DE3) strain according to the plasmid manufacturer protocol available at http://richsingiser.com/4402/Novagen %20pET %20system %20manual.pdf. The incubation temperature for protein production was 30 degrees C., which was found optimal for maximum yield of the active protein. Cells were lysed using lysis buffer (50 mM Tris-HCl pH7.4, 1% Triton X100, 0.5 mM CaCl) and heated at 60 degrees C. for 20 minutes. Coagulated cell debris was removed by centrifugation. The thermostable recombinant pectate lyases were detected in the soluble fraction only, consistent with the notion that they were thermostable enzymes.

Example 5: Pectate Lyase Activity Assay

Pectate lyase activity assay was carried out essentially as described in Takao M, Nakaniwa T, Yoshikawa K, Terashita T, Sakai T., "Purification and characterization of thermostable pectate lyase with protopectinase activity from thermophilic *Bacillus* sp. TS 47". Biosci Biotechnol Biochem. 2000 64:2360-7. In more detail, pectate lyase activity was assayed by measuring the increase in absorbance at 235 nm of the reaction mixture. Polygalacturonic acid (PGA) sodium salt from de-methylated citrus pectin (purchased from MegaZyme) was used as substrate. A reaction mixture containing 1 ml of 0.1% PGA in 10 mM Tris-HCl buffer, pH 8.0 and 0.5 mM CaCl2, and an appropriate amount of enzyme solution was incubated for 30 minutes at 60 degrees C.

The reaction was stopped by placing the mixture in 100 degrees C. (boiling water bath) for 5 min. Relative pectate lyase activity was calculated from the difference in absorption of the reaction mixture at 235 nm at the start and at the end of the reaction.

Example 6: Thermostability of Polypeptides with Pectate Lyase Activity

Thermostability of the polypeptides with pectate lyase activity was determined by pre-incubation for 10 minutes in 50 mM Tris-HCl pH 8.0, either at room temperature (control) or at 70 degrees C., 75 degrees C. and 80 degrees C. before measuring their activity according to example 5.

After pre-incubation, the samples were brought to 60 degrees C., substrate (PGA) was added and samples were assayed for activity as described in Example 5 at 60 degrees C. pH 8.0. Residual activities for each sample were calculated as % of the activity of the sample pre-incubated at room temperature (control sample).

Example 7: Calcium Dependence of Polypeptides with Pectate Lyase Activity

Calcium dependence of the polypeptides with pectate lyase activity was determined according to the method described in example 5 except that calcium was omitted from the reaction mixture, i.e. with and without 0.5 mM CaCl2.

Example 8: Sequences Provided Herein

Amino acid sequence and nucleotide sequences are provided herewith in the WIPO ST_25 standard. For convenience, the sequences are also provided in table 2.

SEQ ID NO: 1 is derived from the prior art and has been disclosed in Takao et al, Biosci. Biotechnol. Biochem. (2000) 64: 2360-2367 and in Takao et al., Biosci. Biotechnol. Biochem. (2001) 65: 322-329.

SEQ ID NO: 2 was obtained by random mutagenesis of the DNA encoding SEQ ID NO: 1 (shown herein as SEQ ID NO: 7) as described in example 2, SEQ ID NO: 3 was obtained by random mutagenesis of the DNA encoding SEQ ID NO: 2 (shown herein as SEQ ID NO: 8). The DNA encoding the polypeptide according to SEQ ID NO: 3 is shown herein as SEQ ID NO: 9. The amino acids deviating from the wild type sequence of SEQ ID NO: 1 are shown in capital letters.

The polypeptide with an amino acid sequence according to SEQ ID NO: 2 is a homologue of the polypeptide according to SEQ ID NO: 1. These two polypeptides have 385 of the 416 amino acids in common, in other words they are 93% identical.

The polypeptide according to SEQ ID NO: 3 is also a homologue of the polypeptide according to SEQ ID NO: 1. These two polypeptides have 369 of the 416 amino acids in common, in other words they are 89% identical.

The polypeptides according to SEQ ID NO:s 4, 5 and 6 are derivable from the polypeptides according to SEQ ID NO:s 1, 2 and 3 respectively, by altering the amino acid corresponding to the amino acid at position 231 in SEQ ID NO: 1 into a leucine residue. The amino acid corresponding to position 231 in SEQ ID NO: 1 is indicated in bold and underlined typeface in table 2.

The nucleotide sequences according to SEQ ID NO:s 10, 11 and 12 encode the polypeptides with the A231L variant according to SEQ ID NO:s 4, 5 and 6 respectively.

The nucleotide sequences according to SEQ ID NO:s 13-16 correspond to the primers used for producing A231L variants from the polypeptides with an amino acid sequence according to SEQ ID NO: 1-3, as detailed in example 3.

TABLE 2

Amino add and nucleotide sequences disclosed herein,

| SEQ ID NO: | | Sequence | | | | | |
|---|---|---|---|---|---|---|---|
| 1 | 1 | kelghevlkp | ydgwaaygeg | ttggamaspg | nvfvvtnrte | liqalggnnh | tnqynsvpki |
| | 61 | iyvkgtidln | vddnnqpvgp | dfykdphfdf | eaylreydpa | twgkkevegp | leearvrsqk |
| | 121 | kqkdrimvyv | gsntsiigvg | kdakikgggf | liknvdnvii | rniefeapld | yfpewdptdg |
| | 181 | tlgewnseyd | sisiegsshi | widhntftdg | dhpdrslgty | fgrpfqqhdg | aldiknssdf |
| | 241 | itisynvftn | hdkvtligas | dsrmadsghl | rvtlhhnyyk | nvtqrlprvr | fgqvhiynny |
| | 301 | yefsnladyd | fqyawgvgvf | sqiyaqnnyf | sfdwdidpsl | iikvwsknee | smyetgtivd |
| | 361 | lpngrryidl | vasynesntl | qlkkevtwkp | mfyhvihptp | svpalvkaka | gagnlh |
| 2 | 1 | kelghDvlkp | ydgwaSygeg | ttggSmaspg | nvYTvtnKte | lVqalggnnh | tnqynsvpki |
| | 61 | iyvkgtiEln | vddnnqpvgp | EfykdphYdf | eaylKeydpK | KwgkkevSgp | leearArsqk |
| | 121 | kqkEriVvNv | gsntsiigvg | kdakiVgggf | liknvdnvii | rniefeapVd | yfpewdptdg |
| | 181 | tlgewnseyd | siTiegsHhi | widhntftdg | dhpDKslgty | fgrpfqqhdg | aldiknssdf |
| | 241 | itisynvfKD | hdkvtligas | dsrmadEghl | rvtlhhnyyk | nvtqrlprvr | fgqvhiynny |
| | 301 | yefsnladyd | fqyawgvgvE | sKiyaqnnyf | sfdwdidpsK | iikvwsknee | smyeSgtivd |
| | 361 | lpngrryidl | vasynesntl | qlkkevGwkp | mfyhvihptp | svpalvkaka | gagnlh |
| 3 | 1 | kelghDvlkp | NdgwaSygeg | ttggSEaspD | nvYTvtnKSe | lVqalggnnh | tnqynsTpki |
| | 61 | iyvkgtiEln | vddnnqpvgp | EYyDdphYdf | eaylKeydpK | KwgkkevSgp | leearArsqk |
| | 121 | kqkEriVvNv | gsntsiigvg | kdakiVgggf | liknvdnvii | rniefeapVd | Ffpewdptdg |
| | 181 | EYgewnseyd | siTieSsHhi | widhntftdg | dhpDKslgty | fgrpfqqhdg | aldiknssdf |
| | 241 | itisynvfKD | hdkvSligSs | dsrKTdEghl | Kvtlhhnyyk | nvtqrlprvr | fgqvhiynny |
| | 301 | yefsnladyd | fqyawgvgvE | sKiyaqnnyf | sfdwdidpsK | iikvwsknee | smyeSgtivd |
| | 361 | lpngrryidl | vasynesntl | qlkkevGwkp | mfyhvihptp | svpalvkaka | gagnlh |

TABLE 2-continued

Amino add and nucleotide sequences disclosed herein,

| SEQ ID NO: | Sequence |
|---|---|
| 4 | 1   kelghevlkp ydgwaaygeg ttggamaspq nvfvvtnrte liqalggnnh tnqynsvpki<br>61  iyvkgtidln vddnnqpvgp dfykdphfdf eaylreydpa twgkkevegp leearvrsqk<br>121 kqkdrimvyv gsntsiigvg kdakikgggf liknvdnvii rniefeapld yfpewdptdg<br>181 tlgewnseyd sisiegsshi widhntftdg dhpdrslgty fgrpfqqhdg lldiknssdf<br>241 itisynvftn hdkvtligas dsrmadsghl rvtlhhnyyk nvtqrlprvr fgqvhiynny<br>301 yefsnladyd fqyawgvgvf sqiyaqnnyf sfdwdidpsl iikvwsknee smyetgtivd<br>361 lpngrryidl vasynesntl qlkkevtwkp mfyhvihptp svpalvkaka gagnlh |
| 5 | 1   kelghDvlkp ydgwaSygeg ttggSmaspq nvYTvtnKte lVqalggnnh tnqynsvpki<br>61  iyvkgtiEln vddnnqpvgp EfykdphYdf eaylKeydpK KwgkkevSgp leearArsqk<br>121 kqkEriVvNv gsntsiigvg kdakiVgggf liknvdnvii rniefeapVd yfpewdptdg<br>181 tlgewnseyd siTiegsHhi widhntftdg dhpdKslgty fgrpfqqhdg lldiknssdf<br>241 itisynvfKD hdkvtligas dsrmadEghl rvtlhhnyyk nvtqrlprvr fgqvhiynny<br>301 yefsnladyd fqyawgvgvE sKiyaqnnyf sfdwdidpsK iikvwsknee smyeSgtivd<br>361 lpngrryidl vasynesntl qlkkevGwkp mfyhvihptp svpalvkaka gagnlh |
| 6 | 1   kelghDvlkp NdgwaSygeg ttggSEaspD nvYTvtnKse lVqalggnnh tnqynsTpki<br>61  iyvkgtiEln vddnnqpvgp EYyDdphYdf eaylKeydpK KwgkkevSgp leearArsqk<br>121 kqkEriVvNv gsntsiigvg kdakiVgggf liknvdnvii rniefeapVd Ffpewdptdg<br>181 EYgewnseyd siTieSsHhi widhntftdg dhpdKslgty fgrpfqqhdg lldiknssdf<br>241 itisynvfKD hdkvSligSs dsrKTdEghl Rvtlhhnyyk nvtqrlprvr fgqvhiynny<br>301 yefsnladyd fqyawgvgvE sKiyaqnnyf sfdwdidpsK iikvwsknee smyeSgtivd<br>361 lpngrryidl vasynesntl qlkkevGwkp mfyhvihptp svpalvkaka gagnlh |
| 7 | aaagaactgg gtcatgaagt tctgaaaccg tatgatggtt gggcagcgta tggtgaaggt    60<br>acaaccggtg gtgcaatggc aagtccgcag aatgtttttg ttgttaccaa tcgtaccgaa   120<br>ctgattcagg cactgggtgg taataatcat accaatcagt ataattccgt gccgaaaatc   180<br>atctatgtga aaggcaccat tgatctgaac gtggatgata taaatcagcc ggttggtccg   240<br>gatttctata agatccgca ttttgatttt gaggcctatc tgcgtgaata tgatccgca    300<br>acctggggta aaaaagaagt tgaaggtccg ctggaagaag cacgcgttcg tagccagaaa   360<br>aaacagaaag atcgtatcat ggtttatgtg ggtagcaaca ccagcattat tggtgttggt   420<br>aaagacgcga aaatcaaagg tggtggtttc ctgattaaaa acgtggataa tgtgatcatc   480<br>cgcaacatcg aatttgaagc accgctggat tattttccgg aatgggatcc gaccgatggc   540<br>accctgggtg aatggaatag cgaatatgat agcattagca ttgaaggcag cagccatatt   600<br>tggattgatc acaataccct taccgatggc gatcatccgg atcgtagcct gggcacctat   660<br>tttggtcgtc cgtttcagca gcatgatggc gcactggata tcaaaaatag cagcgatttt   720<br>atcaccatca gctacaacgt gtttaccaac cacgataaag ttaccctgat tggtgcaagc   780<br>gatagccgta tggcagatag cggtcatctg cgtgttaccc tgcatcacaa ttattacaaa   840<br>aatgttaccc agcgtctgcc tcgtgttcgt tttggtcagg ttcatatcta taacaactac   900<br>tatgagttta gcaacctggc cgattatgat tttcagtatg catggggtgt tggtgtgttt   960<br>agccagattt atgcacagaa caactatttc agcttcgatt gggatattga tccgagccaa  1020<br>attatcaaag tttggagcaa aaatgaagaa agcatgtatg aaaccggcac catcgttgat  1080<br>ctgccgaatg gtcgtcgtta tattgatctg gttgcaagct ataatgaaag caatacctg   1140<br>cagctgaaaa aagaggttac ctggaaaccg atgttctatc atgttattca tccgacccog  1200<br>agcgttccgg cactggttaa agcaaaagcc ggtgcaggta atctgcat               1248 |
| 8 | aaagaactgg gtcatgatgt gctgaaaccg tatgatggtt gggcaagcta tggtgaaggt    60<br>acaaccggtg gtagcatggc aagtccgcag aatgtttata ccgttaccaa taaaaccgaa   120<br>ctggttcagg cactgggtgg taataatcat accaatcagt ataattccgt gccgaaaatc   180<br>atctatgtga aaggcaccat tgaactgaac gtggatgata taaatcagcc ggttggtccg   240<br>gaattctata agatccgca ttatgatttt gaagcctatc tgaaagagta tgatccgaaa   300<br>aaatgggca aaaaagaagt tagcggtccg ctggaagaag cacgcgcacg tagccagaaa   360<br>aaacagaaag aacgtattgt tgtgaatgtg ggtagcaaca ccagcattat tggtgttggt   420<br>aaagatgcca aaattgtgg tggtggtttc ctgattaaaa acgtggataa tgtgatcatc   480<br>cgcaacatcg aatttgaagc accgtggat tattttccgg aatgggatcc gaccgatggc   540<br>accctgggtg aatggaatag cgaatatgat agcattacca ttgaaggcag ccatcatatt   600<br>tggatcgatc acaataccct taccgatggc gatcatccgg ataaaagcct gggcacctat   660<br>tttggtcgtc cgtttcagca gcatgatggc gcactggata tcaaaaatag cagcgatttt   720<br>atcaccatca gctacaacgt gtttaaagac catgataaag tgaccctgat tggtgcaagc   780<br>gatagccgta tggcagatga aggtcatctg cgtgttaccc tgcatcacaa ttattacaaa   840<br>aatgttaccc agcgtctgcc tcgtgttcgt tttggtcagg ttcatatcta taacaactac   900<br>tatgagttta gcaacctggc cgattatgac tttcagtatg catggggtgt tggtgttga   960<br>agcaaaatct atgcccagaa caactatttc agcttcgatt gggatattga cccgagcaaa  1020<br>attatcaaag tttggagcaa aaacgaagaa agcatgtatg aaagcggtac gattgttgat  1080<br>ctgccgaatg gtcgtcgtta tattgatctg gttgcaagct ataatgaaag caatacctg   1140<br>cagctgaaaa aagaggttgg ttggaaaccg atgttctatc atgttattca tccgacccog  1200<br>agcgttccgg cactggttaa agcaaaagcc ggtgcaggta atctgcat               1248 |
| 9 | aaagaactgg gtcatgatgt gctgaaaccg aatgatggtt gggcaagcta tggtgaaggt    60<br>acaaccggtg gtagcgaagc aagtccggat aatgtttata ccgttaccaa taaaagcgaa   120<br>ctggttcagg cactgggtgg taataatcat accaatcagt ataattccac cccgaaaatc   180<br>atctatgtga aaggcaccat tgaactgaac gtggatgata taaatcagcc ggttggtccg   240<br>gaatattatg atgatccgca ttatgatttt gaagcctatc tgaaagagta tgatccgaaa   300<br>aaatgggca aaaaagaagt tagcggtccg ctggaagaag cacgcgcacg tagccagaaa   360<br>aaacagaaag aacgtattgt tgtgaatgtg ggtagcaaca ccagcattat tggtgttggt   420 |

TABLE 2-continued

Amino add and nucleotide sequences disclosed herein,

| SEQ ID NO: | Sequence | |
|---|---|---|
| | aaagatgcca aaattgtggg tggtggtttc ctgattaaaa acgtggataa tgtgatcatc | 480 |
| | cgcaacatcg aatttgaagc accggttgat ttttttccgg aatgggatcc gaccgatggc | 540 |
| | gaatatggcg aatggaatag cgaatatgat agcattacca tcgaaagcag ccatcatatt | 600 |
| | tggatcgatc acaatacctt taccgatggc gatcatccgg ataaaagcct gggcacctat | 660 |
| | tttggtcgtc cgtttcagca gcatgatggc gcactggata tcaaaaatag cagcgatttt | 720 |
| | atcaccatca gctacaacgt gtttaaagac catgataaag tgagcctgat tggttcaagc | 780 |
| | gatagccgta aaaccgatga aggtcatctg aaagttaccc tgcatcacaa ctattacaaa | 840 |
| | aatgttaccc agcgtctgcc tcgtgttcgt tttggtcagg ttcatatcta taacaactac | 900 |
| | tatgagttta gcaacctggc cgattatgac tttcagtatg catggggtgt tggtgttgaa | 960 |
| | agcaaaatct atgcccagaa caactatttc agcttcgatt gggatattga cccgagcaaa | 1020 |
| | attatcaaag tttggagcaa aaacgaagaa agcatgtatg aaagcggtac gattgttgat | 1080 |
| | ctgccgaatg gtcgtcgtta tattgatctg gttgcaagct ataatgaaag caataccctg | 1140 |
| | cagctgaaaa aagaggttgg ttggaaaccg atgttctatc atgttattca tccgacccog | 1200 |
| | agcgttccgg cactggttaa agcaaaagcc ggtgcaggta atctgcat | 1248 |
| 10 | aaagaactgg gtcatgaagt tctgaaaccg tatgatggtt gggcagcgta tggtgaaggt | 60 |
| | acaaccggtg gtgcaatggc aagtccgcag aatgtttttg ttgttaccaa tcgtaccgaa | 120 |
| | ctgattcagg cactgggtgg taataatcat accaatcagt ataattccgt gccgaaaatc | 180 |
| | atctatgtga aaggcaccat tgatctgaac gtggatgata ataatcagcc ggttggtccg | 240 |
| | gatttctata agatccgca ttttgatttt gaggcctatc tgcgtgaata tgatccggca | 300 |
| | acctggggta aaaaagaagt tgaaggtccg ctggaagaag cacgcgttcg tagccagaaa | 360 |
| | aaacagaaag atcgtatcat ggtttatgtg ggtagcaaca ccagcattat tggtgttggt | 420 |
| | aaagacgcga aaatcaaagg tggtggtttc ctgattaaaa acgtggataa tgtgatcatc | 480 |
| | cgcaacatcg aatttgaagc accgctggat tattttccgg aatgggatcc gaccgatggc | 540 |
| | accctgggtg aatggaatag cgaatatgat agcattagca ttgaaggcag cagccatatt | 600 |
| | tggattgatc acaatacctt taccgatggc gatcatccgg atcgtagcct gggcacctat | 660 |
| | tttggtcgtc cgtttcagca gcatgatggc ctgctggata tcaaaaatag cagcgatttt | 720 |
| | atcaccatca gctacaacgt gtttaccaac cacgataaag ttaccctgat tggtgcaagc | 780 |
| | gatagccgta tggcagatag cggtcatctg cgtgttaccc tgcatcacaa ttattacaaa | 840 |
| | aatgttaccc agcgtctgcc tcgtgttcgt tttggtcagg ttcatatcta taacaactac | 900 |
| | tatgagttta gcaacctggc cgattatgat tttcagtatg catggggtgt tggtgtgttt | 960 |
| | agccagattt atgcacagaa caactatttc agcttcgatt gggatattga cccgagcctg | 1020 |
| | attatcaaag tttggagcaa aaatgaagaa agcatgtatg aaaccggcac catcgttgat | 1080 |
| | ctgccgaatg gtcgtcgtta tattgatctg gttgcaagct ataatgaaag caataccctg | 1140 |
| | cagctgaaaa aagaggttac ctggaaaccg atgttctatc atgttattca tccgacccog | 1200 |
| | agcgttccgg cactggttaa agcaaaagcc ggtgcaggta atctgcat | 1248 |
| 11 | aaagaactgg gtcatgatgt gctgaaaccg tatgatggtt gggcaagcta tggtgaaggt | 60 |
| | acaaccggtg gtagcatggc aagtccgcag aatgtttata ccgttaccaa taaaaccgaa | 120 |
| | ctggttcagg cactgggtgg taataatcat accaatcagt ataattccgt gccgaaaatc | 180 |
| | atctatgtga aaggcaccat tgaactgaac gtggatgata ataatcagcc ggttggtccg | 240 |
| | gaattctata aagatccgca ttatgatttt gaagcctatc tgaaagagta tgatccgaaa | 300 |
| | aaatgggca aaaaagaagt tagcggtccg ctggaagaag cacgcgcacg tagccagaaa | 360 |
| | aaacagaaag aacgtattgt tgtgaatgtg ggtagcaaca ccagcattat tggtgttggt | 420 |
| | aaagatgcca aaattgtggg tggtggtttc ctgattaaaa acgtggataa tgtgatcatc | 480 |
| | cgcaacatcg aatttgaagc accggtggdt tattttccgg aatgggatcc gaccgatggc | 540 |
| | accctgggtg aatggaatag cgaatatgat agcattacca ttgaaggcag ccatcatatt | 600 |
| | tggatcgatc acaatacctt taccgatggc gatcatccgg ataaaagcct gggcacctat | 660 |
| | tttggtcgtc cgtttcagca gcatgatggc ctgctggata tcaaaaatag cagcgatttt | 720 |
| | atcaccatca gctacaacgt gtttaaagac catgataaag tgaccctgat tggtgcaagc | 780 |
| | gatagccgta tggcagatga aggtcatctg cgtgttaccc tgcatcacaa ttattacaaa | 840 |
| | aatgttaccc agcgtctgcc tcgtgttcgt tttggtcagg ttcatatcta taacaactac | 900 |
| | tatgagttta gcaacctggc cgattatgac tttcagtatg catggggtgt tggtgttgaa | 960 |
| | agcaaaatct atgcccagaa caactatttc agcttcgatt gggatattga cccgagcaaa | 1020 |
| | attatcaaag tttggagcaa aaacgaagaa agcatgtatg aaagcggtac gattgttgat | 1080 |
| | ctgccgaatg gtcgtcgtta tattgatctg gttgcaagct ataatgaaag caataccctg | 1140 |
| | cagctgaaaa aagaggttgg ttggaaaccg atgttctatc atgttattca tccgacccog | 1200 |
| | agcgttccgg cactggttaa agcaaaagcc ggtgcaggta atctgcat | 1248 |
| 12 | aaagaactgg gtcatgatgt gctgaaaccg aatgatggtt gggcaagcta tggtgaaggt | 60 |
| | acaaccggtg gtagcgaaga aagtccggat aatgtttata ccgttaccaa taaaagcgaa | 120 |
| | ctagttcagg cactggatag taataatcat accaatcagt ataattccac cccgaaaatc | 180 |
| | atctatgtga aaggcaccat tgaactgaac gtggatgata ataatcagcc ggttggtccg | 240 |
| | gaatattatg atgatccgca ttatgatttt gaagcctatc tgaaagagta tgatccggca | 300 |
| | aaatgggca aaaaagaagt tagcggtccg ctggaagaag cacgcgcacg tagccagaaa | 360 |
| | aaacagaaag aacgtattgt tgtgaatgtg ggtagcaaca ccagcattat tggtgttggt | 420 |
| | aaagatgcca aaattgtagg tggtggtttc ctgattaaaa acgtggataa tgtgatcatc | 480 |
| | cgcaacatcg aatttgaaga accggttgat ttttttccgg aatgggatcc gaccgatggt | 540 |
| | aaatatgcg aatggaatag cgaatatgat agcattacca tcgaaagcag ccatcatatt | 600 |
| | tggatcgatc acaatacctt taccgatggc gatcatccgg ataaaagcct gggcacctat | 660 |
| | tttggtcgtc cgtttaagaa gcatgatggc ctgctgata tcaaaaatag cagcgattag | 720 |
| | atcaccatca gctacaacgt gtttaaagac catgataaag tgagcctgat tagttcaagc | 780 |
| | gatagccgta aaaccgatga aggtcatctg aaagttaccc tgcatcacaa ctattacaaa | 840 |
| | aatgttaccc agcgtctgcc tcgtgttcgt tttgatcagg ttcatatcta taacaactac | 900 |
| | tatgagttta gcaacctgac cgattatgac tttcaatatg catggggtgt tgatgttgaa | 960 |
| | agcaaaatct atgcccagaa caactatttc agttcgatt gggatattga cccgagcaaa | 1020 |

TABLE 2-continued

Amino add and nucleotide sequences disclosed herein,

| SEQ ID NO: | Sequence | |
|---|---|---|
| | attatcaaag tttggagcaa aaacgaagaa agcatgtatg aaagcggtac gattgttgat | 1080 |
| | ctgccgaatg gtcgtcgtta tattgatctg gttgcaagct ataatgaaag caatacccctg | 1140 |
| | cagctgaaaa aagaggttgg ttggaaaccg atgttctatc atgttattca tccgaccccg | 1200 |
| | agcgttccgg cactggttaa agcaaaagcc ggtgaaggta atctgcat | 1248 |
| 13 | gaaattaata cgactcacta tagg | |
| 14 | gccatcatgc tgctgaaacg gacgaccaaa ataggtg | |
| 15 | gatcgtccgt ttcagcaaca tgatggcctg ctagatatc | |
| 16 | ggttatgcta gattattctc agaggtg | |

The invention claimed is:

1. A polypeptide with pectate lyase activity, the polypeptide comprising:
   an amino acid sequence that is at least 70% identical to the amino acid according to SEQ ID NO: 1, and
   a leucine residue at an amino acid position corresponding to position 231 in SEQ ID NO: 1.

2. The polypeptide of claim 1, wherein the polypeptide comprises an amino acid sequence that is at least 75% identical to the amino acid according to SEQ ID NO: 1.

3. A composition comprising the polypeptide of claim 1.

4. A nucleic acid encoding the polypeptide of claim 1.

5. A vector comprising the nucleic acid of claim 4.

6. A composition comprising the nucleic acid of claim 4.

7. A recombinant host cell comprising the nucleic acid of claim 4.

8. The recombinant host cell of claim 7, wherein the host cell is selected from the group consisting of *Escherichia coli*, *Bacillus*, *Corynebacterium*, *Pseudomonas*, *Pichia pastoris*, *Saccharomyces cerevisiae*, *Yarrowia lipolytica*, filamentous fungi, yeast, and insect cells.

9. A method for producing the polypeptide of claim 1, the method comprising:
   culturing the recombinant host cell of claim 7 under conditions suitable for the production of the polypeptide, and
   recovering the polypeptide obtained, and
   optionally purifying said polypeptide.

10. A method for improving the thermostability of a polypeptide with pectate lyase activity comprising an amino acid sequence that is at least 90% identical to the amino acid according to SEQ ID NO: 1, the method comprising:
   altering the amino acid at a position corresponding to position 231 in SEQ ID NO: 1 to a leucine residue;
   wherein the polypeptide comprising a leucine residue at a position corresponding to position 231 in SEQ ID NO: 1 has an improved thermostability as compared to the pectate lyase of SEQ ID NO: 1.

11. A method for decreasing, abolishing or removing the calcium dependence of a polypeptide with pectate lyase activity comprising an amino acid sequence that is at least 90% identical to the amino acid according to SEQ ID NO: 1, the method comprising:
   altering the amino acid at a position corresponding to position 231 in SEQ ID NO: 1 to a leucine residue.

12. A composition comprising the vector of claim 5.

13. A recombinant host cell comprising the vector of claim 5.

14. The polypeptide of claim 1, wherein the polypeptide comprises an amino acid sequence that is at least 80% identical to the amino acid according to SEQ ID NO: 1.

15. The polypeptide of claim 1, wherein the polypeptide comprises an amino acid sequence that is at least 85% identical to the amino acid according to SEQ ID NO: 1.

16. The polypeptide of claim 1, wherein the polypeptide comprises an amino acid sequence that is at least 90% identical to the amino acid according to SEQ ID NO: 1.

17. The polypeptide of claim 1, wherein the polypeptide comprises an amino acid sequence that is at least 95% identical to the amino acid according to SEQ ID NO: 1.

18. The polypeptide of claim 1, wherein the polypeptide comprises an amino acid sequence that is at least 97% identical to the amino acid according to SEQ ID NO: 1.

19. The polypeptide of claim 1, wherein the polypeptide comprises an amino acid sequence that is at least 98% identical to the amino acid according to SEQ ID NO: 1.

20. The polypeptide of claim 1, wherein the polypeptide comprises an amino acid sequence that is identical to the amino acid according to SEQ ID NO: 1 except for a leucine at a position corresponding to position 231 of SEQ ID NO: 1.

21. The polypeptide of claim 16,
   wherein the polypeptide has pectate lyase activity, and
   wherein the pectate lyase activity is calcium-independent and/or wherein the polypeptide has an improved thermostability as compared to the pectate lyase of SEQ ID NO: 1.

* * * * *

SEQUENCE LISTING

<160> NUMBER OF SEQ ID NOS: 16

<210> SEQ ID NO 1
<211> LENGTH: 416
<212> TYPE: PRT
<213> ORGANISM: Bacillus spec.

<400> SEQUENCE: 1

Lys Glu Leu Gly His Glu Val Leu Lys Pro Tyr Asp Gly Trp Ala Ala
1               5                   10                  15

Tyr Gly Glu Gly Thr Thr Gly Gly Ala Met Ala Ser Pro Gln Asn Val
            20                  25                  30

Phe Val Val Thr Asn Arg Thr Glu Leu Ile Gln Ala Leu Gly Gly Asn
        35                  40                  45

Asn His Thr Asn Gln Tyr Asn Ser Val Pro Lys Ile Ile Tyr Val Lys
    50                  55                  60

Gly Thr Ile Asp Leu Asn Val Asp Asp Asn Gln Pro Val Gly Pro
65                  70                  75                  80

Asp Phe Tyr Lys Asp Pro His Phe Asp Phe Glu Ala Tyr Leu Arg Glu
                85                  90                  95

Tyr Asp Pro Ala Thr Trp Gly Lys Lys Glu Val Glu Gly Pro Leu Glu
            100                 105                 110

Glu Ala Arg Val Arg Ser Gln Lys Lys Gln Lys Asp Arg Ile Met Val
        115                 120                 125

Tyr Val Gly Ser Asn Thr Ser Ile Ile Gly Val Gly Lys Asp Ala Lys
    130                 135                 140

Ile Lys Gly Gly Gly Phe Leu Ile Lys Asn Val Asp Asn Val Ile Ile
145                 150                 155                 160

Arg Asn Ile Glu Phe Glu Ala Pro Leu Asp Tyr Phe Pro Glu Trp Asp
                165                 170                 175

Pro Thr Asp Gly Thr Leu Gly Glu Trp Asn Ser Glu Tyr Asp Ser Ile
            180                 185                 190

Ser Ile Glu Gly Ser Ser His Ile Trp Ile Asp His Asn Thr Phe Thr
        195                 200                 205

Asp Gly Asp His Pro Asp Arg Ser Leu Gly Thr Tyr Phe Gly Arg Pro
    210                 215                 220

Phe Gln Gln His Asp Gly Ala Leu Asp Ile Lys Asn Ser Ser Asp Phe
225                 230                 235                 240

Ile Thr Ile Ser Tyr Asn Val Phe Thr Asn His Asp Lys Val Thr Leu
                245                 250                 255

Ile Gly Ala Ser Asp Ser Arg Met Ala Asp Ser Gly His Leu Arg Val
            260                 265                 270

Thr Leu His His Asn Tyr Tyr Lys Asn Val Thr Gln Arg Leu Pro Arg
            275                 280                 285

Val Arg Phe Gly Gln Val His Ile Tyr Asn Asn Tyr Tyr Glu Phe Ser
290                 295                 300

Asn Leu Ala Asp Tyr Asp Phe Gln Tyr Ala Trp Gly Val Gly Val Phe
305                 310                 315                 320

Ser Gln Ile Tyr Ala Gln Asn Asn Tyr Phe Ser Phe Asp Trp Asp Ile
                325                 330                 335

Asp Pro Ser Leu Ile Ile Lys Val Trp Ser Lys Asn Glu Glu Ser Met
            340                 345                 350

Tyr Glu Thr Gly Thr Ile Val Asp Leu Pro Asn Gly Arg Arg Tyr Ile
            355                 360                 365

Asp Leu Val Ala Ser Tyr Asn Glu Ser Asn Thr Leu Gln Leu Lys Lys
            370                 375                 380

Glu Val Thr Trp Lys Pro Met Phe Tyr His Val Ile His Pro Thr Pro
385                 390                 395                 400

Ser Val Pro Ala Leu Val Lys Ala Lys Ala Gly Ala Gly Asn Leu His
                405                 410                 415

<210> SEQ ID NO 2
<211> LENGTH: 416
<212> TYPE: PRT
<213> ORGANISM: Bacillus spec.

<400> SEQUENCE: 2

Lys Glu Leu Gly His Asp Val Leu Lys Pro Tyr Asp Gly Trp Ala Ser
1               5                   10                  15

Tyr Gly Glu Gly Thr Thr Gly Gly Ser Met Ala Ser Pro Gln Asn Val
            20                  25                  30

Tyr Thr Val Thr Asn Lys Thr Glu Leu Val Gln Ala Leu Gly Gly Asn
            35                  40                  45

Asn His Thr Asn Gln Tyr Asn Ser Val Pro Lys Ile Ile Tyr Val Lys
50                  55                  60

Gly Thr Ile Glu Leu Asn Val Asp Asp Asn Asn Gln Pro Val Gly Pro
65                  70                  75                  80

Glu Phe Tyr Lys Asp Pro His Tyr Asp Phe Glu Ala Tyr Leu Lys Glu
                85                  90                  95

Tyr Asp Pro Lys Lys Trp Gly Lys Lys Glu Val Ser Gly Pro Leu Glu
            100                 105                 110

Glu Ala Arg Ala Arg Ser Gln Lys Lys Gln Lys Glu Arg Ile Val Val
            115                 120                 125

Asn Val Gly Ser Asn Thr Ser Ile Ile Gly Val Gly Lys Asp Ala Lys
            130                 135                 140

Ile Val Gly Gly Gly Phe Leu Ile Lys Asn Val Asp Asn Val Ile Ile
145                 150                 155                 160

Arg Asn Ile Glu Phe Glu Ala Pro Val Asp Tyr Phe Pro Glu Trp Asp
                165                 170                 175

Pro Thr Asp Gly Thr Leu Gly Glu Trp Asn Ser Glu Tyr Asp Ser Ile
            180                 185                 190

Thr Ile Glu Gly Ser His His Ile Trp Ile Asp His Asn Thr Phe Thr
            195                 200                 205

Asp Gly Asp His Pro Asp Lys Ser Leu Gly Thr Tyr Phe Gly Arg Pro

```
                210                 215                 220
        Phe Gln Gln His Asp Gly Ala Leu Asp Ile Lys Asn Ser Ser Asp Phe
        225                 230                 235                 240

Ile Thr Ile Ser Tyr Asn Val Phe Lys Asp His Asp Lys Val Thr Leu
                        245                 250                 255

Ile Gly Ala Ser Asp Ser Arg Met Ala Asp Glu Gly His Leu Arg Val
                        260                 265                 270

Thr Leu His His Asn Tyr Tyr Lys Asn Val Thr Gln Arg Leu Pro Arg
                        275                 280                 285

Val Arg Phe Gly Gln Val His Ile Tyr Asn Asn Tyr Glu Phe Ser
        290                 295                 300

Asn Leu Ala Asp Tyr Asp Phe Gln Tyr Ala Trp Val Gly Val Glu
        305                 310                 315                 320

Ser Lys Ile Tyr Ala Gln Asn Asn Tyr Phe Ser Phe Asp Trp Asp Ile
                        325                 330                 335

Asp Pro Ser Lys Ile Ile Lys Val Trp Ser Lys Asn Glu Glu Ser Met
                        340                 345                 350

Tyr Glu Ser Gly Thr Ile Val Asp Leu Pro Asn Gly Arg Arg Tyr Ile
                        355                 360                 365

Asp Leu Val Ala Ser Tyr Asn Glu Ser Asn Thr Leu Gln Leu Lys Lys
                        370                 375                 380

Glu Val Gly Trp Lys Pro Met Phe Tyr His Val Ile His Pro Thr Pro
        385                 390                 395                 400

Ser Val Pro Ala Leu Val Lys Ala Lys Ala Gly Ala Gly Asn Leu His
                        405                 410                 415

<210> SEQ ID NO 3
<211> LENGTH: 416
<212> TYPE: PRT
<213> ORGANISM: Bacillus spec.

<400> SEQUENCE: 3

Lys Glu Leu Gly His Asp Val Leu Lys Pro Asn Asp Gly Trp Ala Ser
1               5                   10                  15

Tyr Gly Glu Gly Thr Thr Gly Gly Ser Glu Ala Ser Pro Asp Asn Val
                20                  25                  30

Tyr Thr Val Thr Asn Lys Ser Glu Leu Val Gln Ala Leu Gly Gly Asn
                35                  40                  45

Asn His Thr Asn Gln Tyr Asn Ser Thr Pro Lys Ile Ile Tyr Val Lys
50                  55                  60

Gly Thr Ile Glu Leu Asn Val Asp Asp Asn Gln Pro Val Gly Pro
65                  70                  75                  80

Glu Tyr Tyr Asp Asp Pro His Tyr Asp Phe Glu Ala Tyr Leu Lys Glu
                85                  90                  95

Tyr Asp Pro Lys Lys Trp Gly Lys Lys Glu Val Ser Gly Pro Leu Glu
                100                 105                 110

Glu Ala Arg Ala Arg Ser Gln Lys Gln Lys Glu Arg Ile Val Val
                115                 120                 125

Asn Val Gly Ser Asn Thr Ser Ile Ile Gly Val Gly Lys Asp Ala Lys
                130                 135                 140

Ile Val Gly Gly Gly Phe Leu Ile Lys Asn Val Asp Asn Val Ile Ile
145                 150                 155                 160

Arg Asn Ile Glu Phe Glu Ala Pro Val Asp Phe Phe Pro Glu Trp Asp
                165                 170                 175
```

```
Pro Thr Asp Gly Glu Tyr Gly Glu Trp Asn Ser Glu Tyr Asp Ser Ile
            180                 185                 190

Thr Ile Glu Ser Ser His His Ile Trp Ile Asp His Asn Thr Phe Thr
        195                 200                 205

Asp Gly Asp His Pro Asp Lys Ser Leu Gly Thr Tyr Phe Gly Arg Pro
    210                 215                 220

Phe Gln Gln His Asp Gly Ala Leu Asp Ile Lys Asn Ser Ser Asp Phe
225                 230                 235                 240

Ile Thr Ile Ser Tyr Asn Val Phe Lys Asp His Asp Lys Val Ser Leu
                245                 250                 255

Ile Gly Ser Ser Asp Ser Arg Lys Thr Asp Glu Gly His Leu Lys Val
            260                 265                 270

Thr Leu His His Asn Tyr Tyr Lys Asn Val Thr Gln Arg Leu Pro Arg
        275                 280                 285

Val Arg Phe Gly Gln Val His Ile Tyr Asn Asn Tyr Glu Phe Ser
    290                 295                 300

Asn Leu Ala Asp Tyr Asp Phe Gln Tyr Ala Trp Gly Val Gly Val Glu
305                 310                 315                 320

Ser Lys Ile Tyr Ala Gln Asn Asn Tyr Phe Ser Phe Asp Trp Asp Ile
                325                 330                 335

Asp Pro Ser Lys Ile Ile Lys Val Trp Ser Lys Asn Glu Glu Ser Met
            340                 345                 350

Tyr Glu Ser Gly Thr Ile Val Asp Leu Pro Asn Gly Arg Arg Tyr Ile
        355                 360                 365

Asp Leu Val Ala Ser Tyr Asn Glu Ser Asn Thr Leu Gln Leu Lys Lys
    370                 375                 380

Glu Val Gly Trp Lys Pro Met Phe Tyr His Val Ile His Pro Thr Pro
385                 390                 395                 400

Ser Val Pro Ala Leu Val Lys Ala Lys Ala Gly Ala Gly Asn Leu His
                405                 410                 415

<210> SEQ ID NO 4
<211> LENGTH: 416
<212> TYPE: PRT
<213> ORGANISM: Bacillus spec.

<400> SEQUENCE: 4

Lys Glu Leu Gly His Glu Val Leu Lys Pro Tyr Asp Gly Trp Ala Ala
1               5                   10                  15

Tyr Gly Glu Gly Thr Thr Gly Gly Ala Met Ala Ser Pro Gln Asn Val
            20                  25                  30

Phe Val Val Thr Asn Arg Thr Glu Leu Ile Gln Ala Leu Gly Gly Asn
        35                  40                  45

Asn His Thr Asn Gln Tyr Asn Ser Val Pro Lys Ile Ile Tyr Val Lys
    50                  55                  60

Gly Thr Ile Asp Leu Asn Val Asp Asp Asn Gln Pro Val Gly Pro
65                  70                  75                  80

Asp Phe Tyr Lys Asp Pro His Phe Asp Phe Glu Ala Tyr Leu Arg Glu
                85                  90                  95

Tyr Asp Pro Ala Thr Trp Gly Lys Lys Glu Val Glu Gly Pro Leu Glu
            100                 105                 110

Glu Ala Arg Val Arg Ser Gln Lys Lys Gln Lys Asp Arg Ile Met Val
        115                 120                 125

Tyr Val Gly Ser Asn Thr Ser Ile Ile Gly Val Gly Lys Asp Ala Lys
    130                 135                 140
```

```
Ile Lys Gly Gly Gly Phe Leu Ile Lys Asn Val Asp Asn Val Ile Ile
145                 150                 155                 160

Arg Asn Ile Glu Phe Glu Ala Pro Leu Asp Tyr Phe Pro Glu Trp Asp
                165                 170                 175

Pro Thr Asp Gly Thr Leu Gly Glu Trp Asn Ser Glu Tyr Asp Ser Ile
            180                 185                 190

Ser Ile Glu Gly Ser Ser His Ile Trp Ile Asp His Asn Thr Phe Thr
        195                 200                 205

Asp Gly Asp His Pro Asp Arg Ser Leu Gly Thr Tyr Phe Gly Arg Pro
    210                 215                 220

Phe Gln Gln His Asp Gly Leu Leu Asp Ile Lys Asn Ser Ser Asp Phe
225                 230                 235                 240

Ile Thr Ile Ser Tyr Asn Val Phe Thr Asn His Asp Lys Val Thr Leu
                245                 250                 255

Ile Gly Ala Ser Asp Ser Arg Met Ala Asp Ser Gly His Leu Arg Val
            260                 265                 270

Thr Leu His His Asn Tyr Tyr Lys Asn Val Thr Gln Arg Leu Pro Arg
        275                 280                 285

Val Arg Phe Gly Gln Val His Ile Tyr Asn Asn Tyr Glu Phe Ser
    290                 295                 300

Asn Leu Ala Asp Tyr Asp Phe Gln Tyr Ala Trp Gly Val Gly Val Phe
305                 310                 315                 320

Ser Gln Ile Tyr Ala Gln Asn Asn Tyr Phe Ser Phe Asp Trp Asp Ile
                325                 330                 335

Asp Pro Ser Leu Ile Ile Lys Val Trp Ser Lys Asn Glu Glu Ser Met
            340                 345                 350

Tyr Glu Thr Gly Thr Ile Val Asp Leu Pro Asn Gly Arg Arg Tyr Ile
        355                 360                 365

Asp Leu Val Ala Ser Tyr Asn Glu Ser Asn Thr Leu Gln Leu Lys Lys
    370                 375                 380

Glu Val Thr Trp Lys Pro Met Phe Tyr His Val Ile His Pro Thr Pro
385                 390                 395                 400

Ser Val Pro Ala Leu Val Lys Ala Lys Ala Gly Ala Gly Asn Leu His
                405                 410                 415
```

<210> SEQ ID NO 5
<211> LENGTH: 416
<212> TYPE: PRT
<213> ORGANISM: Bacillus spec.

<400> SEQUENCE: 5

```
Lys Glu Leu Gly His Asp Val Leu Lys Pro Tyr Asp Gly Trp Ala Ser
1               5                   10                  15

Tyr Gly Glu Gly Thr Thr Gly Gly Ser Met Ala Ser Pro Gln Asn Val
                20                  25                  30

Tyr Thr Val Thr Asn Lys Thr Glu Leu Val Gln Ala Leu Gly Gly Asn
            35                  40                  45

Asn His Thr Asn Gln Tyr Asn Ser Val Pro Lys Ile Ile Tyr Val Lys
    50                  55                  60

Gly Thr Ile Glu Leu Asn Val Asp Asp Asn Asn Gln Pro Val Gly Pro
65                  70                  75                  80

Glu Phe Tyr Lys Asp Pro His Tyr Asp Phe Glu Ala Tyr Leu Lys Glu
                85                  90                  95

Tyr Asp Pro Lys Lys Trp Gly Lys Lys Glu Val Ser Gly Pro Leu Glu
```

```
            100                 105                 110
Glu Ala Arg Ala Arg Ser Gln Lys Lys Gln Lys Glu Arg Ile Val Val
            115                 120                 125
Asn Val Gly Ser Asn Thr Ser Ile Ile Gly Val Gly Lys Asp Ala Lys
130                 135                 140
Ile Val Gly Gly Gly Phe Leu Ile Lys Asn Val Asp Asn Val Ile Ile
145                 150                 155                 160
Arg Asn Ile Glu Phe Glu Ala Pro Val Asp Tyr Phe Pro Glu Trp Asp
                165                 170                 175
Pro Thr Asp Gly Thr Leu Gly Glu Trp Asn Ser Glu Tyr Asp Ser Ile
                180                 185                 190
Thr Ile Glu Gly Ser His His Ile Trp Ile Asp His Asn Thr Phe Thr
                195                 200                 205
Asp Gly Asp His Pro Asp Lys Ser Leu Gly Thr Tyr Phe Gly Arg Pro
                210                 215                 220
Phe Gln Gln His Asp Gly Leu Leu Asp Ile Lys Asn Ser Ser Asp Phe
225                 230                 235                 240
Ile Thr Ile Ser Tyr Asn Val Phe Lys Asp His Asp Lys Val Thr Leu
                245                 250                 255
Ile Gly Ala Ser Asp Ser Arg Met Ala Asp Glu Gly His Leu Arg Val
                260                 265                 270
Thr Leu His His Asn Tyr Tyr Lys Asn Val Thr Gln Arg Leu Pro Arg
                275                 280                 285
Val Arg Phe Gly Gln Val His Ile Tyr Asn Asn Tyr Tyr Glu Phe Ser
                290                 295                 300
Asn Leu Ala Asp Tyr Asp Phe Gln Tyr Ala Trp Gly Val Gly Val Glu
305                 310                 315                 320
Ser Lys Ile Tyr Ala Gln Asn Asn Tyr Phe Ser Phe Asp Trp Asp Ile
                325                 330                 335
Asp Pro Ser Lys Ile Ile Lys Val Trp Ser Lys Asn Glu Glu Ser Met
                340                 345                 350
Tyr Glu Ser Gly Thr Ile Val Asp Leu Pro Asn Gly Arg Arg Tyr Ile
                355                 360                 365
Asp Leu Val Ala Ser Tyr Asn Glu Ser Asn Thr Leu Gln Leu Lys Lys
                370                 375                 380
Glu Val Gly Trp Lys Pro Met Phe Tyr His Val Ile His Pro Thr Pro
385                 390                 395                 400
Ser Val Pro Ala Leu Val Lys Ala Lys Ala Gly Ala Gly Asn Leu His
                405                 410                 415

<210> SEQ ID NO 6
<211> LENGTH: 416
<212> TYPE: PRT
<213> ORGANISM: Bacillus spec.

<400> SEQUENCE: 6

Lys Glu Leu Gly His Asp Val Leu Lys Pro Asn Asp Gly Trp Ala Ser
1               5                   10                  15
Tyr Gly Glu Gly Thr Thr Gly Gly Ser Glu Ala Ser Pro Asp Asn Val
                20                  25                  30
Tyr Thr Val Thr Asn Lys Ser Glu Leu Val Gln Ala Leu Gly Gly Asn
                35                  40                  45
Asn His Thr Asn Gln Tyr Asn Ser Thr Pro Lys Ile Ile Tyr Val Lys
50                  55                  60
```

Gly Thr Ile Glu Leu Asn Val Asp Asp Asn Asn Gln Pro Val Gly Pro
65                  70                  75                  80

Glu Tyr Tyr Asp Asp Pro His Tyr Asp Phe Glu Ala Tyr Leu Lys Glu
                85                  90                  95

Tyr Asp Pro Lys Lys Trp Gly Lys Lys Glu Val Ser Gly Pro Leu Glu
            100                 105                 110

Glu Ala Arg Ala Arg Ser Gln Lys Lys Gln Lys Glu Arg Ile Val Val
        115                 120                 125

Asn Val Gly Ser Asn Thr Ser Ile Ile Gly Val Gly Lys Asp Ala Lys
130                 135                 140

Ile Val Gly Gly Gly Phe Leu Ile Lys Asn Val Asp Asn Val Ile Ile
145                 150                 155                 160

Arg Asn Ile Glu Phe Glu Ala Pro Val Asp Phe Phe Pro Glu Trp Asp
                165                 170                 175

Pro Thr Asp Gly Glu Tyr Gly Glu Trp Asn Ser Glu Tyr Asp Ser Ile
            180                 185                 190

Thr Ile Glu Ser Ser His His Ile Trp Ile Asp His Asn Thr Phe Thr
        195                 200                 205

Asp Gly Asp His Pro Asp Lys Ser Leu Gly Thr Tyr Phe Gly Arg Pro
210                 215                 220

Phe Gln Gln His Asp Gly Leu Leu Asp Ile Lys Asn Ser Ser Asp Phe
225                 230                 235                 240

Ile Thr Ile Ser Tyr Asn Val Phe Lys Asp His Asp Lys Val Ser Leu
                245                 250                 255

Ile Gly Ser Ser Asp Ser Arg Lys Thr Asp Glu Gly His Leu Lys Val
            260                 265                 270

Thr Leu His His Asn Tyr Tyr Lys Asn Val Thr Gln Arg Leu Pro Arg
        275                 280                 285

Val Arg Phe Gly Gln Val His Ile Tyr Asn Asn Tyr Tyr Glu Phe Ser
290                 295                 300

Asn Leu Ala Asp Tyr Asp Phe Gln Tyr Ala Trp Gly Val Gly Val Glu
305                 310                 315                 320

Ser Lys Ile Tyr Ala Gln Asn Asn Tyr Phe Ser Phe Asp Trp Asp Ile
                325                 330                 335

Asp Pro Ser Lys Ile Ile Lys Val Trp Ser Lys Asn Glu Glu Ser Met
            340                 345                 350

Tyr Glu Ser Gly Thr Ile Val Asp Leu Pro Asn Gly Arg Arg Tyr Ile
        355                 360                 365

Asp Leu Val Ala Ser Tyr Asn Glu Ser Asn Thr Leu Gln Leu Lys Lys
370                 375                 380

Glu Val Gly Trp Lys Pro Met Phe Tyr His Val Ile His Pro Thr Pro
385                 390                 395                 400

Ser Val Pro Ala Leu Val Lys Ala Lys Ala Gly Ala Gly Asn Leu His
                405                 410                 415

<210> SEQ ID NO 7
<211> LENGTH: 1248
<212> TYPE: DNA
<213> ORGANISM: Bacillus spec.

<400> SEQUENCE: 7
aaagaactgg gtcatgaagt tctgaaaccg tatgatggtt gggcagcgta tggtgaaggt    60
acaaccggtg gtgcaatggc aagtccgcag aatgtttttg ttgttaccaa tcgtaccgaa   120
ctgattcagg cactgggtgg taataatcat accaatcagt ataattccgt gccgaaaatc   180

-continued

```
atctatgtga aaggcaccat tgatctgaac gtggatgata ataatcagcc ggttggtccg      240
gatttctata aagatccgca ttttgatttt gaggcctatc tgcgtgaata tgatccggca      300
acctggggta aaaagaagt tgaaggtccg ctggaagaag cacgcgttcg tagccagaaa       360
aaacagaaag atcgtatcat ggtttatgtg ggtagcaaca ccagcattat tggtgttggt      420
aaagacgcga aaatcaaagg tggtggtttc ctgattaaaa acgtggataa tgtgatcatc      480
cgcaacatcg aatttgaagc accgctggat tattttccgg aatgggatcc gaccgatggc      540
accctgggtg aatggaatag cgaatatgat agcattagca ttgaaggcag cagccatatt      600
tggattgatc acaataccct taccgatggc gatcatccgg atcgtagcct gggcaccctat     660 tttggtcgtc cgtttcagca gcatgatggc gcactggata tcaaaaatag cagcgatttt     720
atcaccatca gctacaacgt gtttaccaac cacgataaag ttaccctgat tggtgcaagc     780
gatagccgta tggcagatag cggtcatctg cgtgttaccc tgcatcacaa ttattacaaa     840
aatgttaccc agcgtctgcc tcgtgttcgt tttggtcagg ttcatatcta taacaactac     900
tatgagttta gcaacctggc cgattatgat tttcagtatg catggggtgt tggtgtgttt     960
agccagattt atgcacagaa caactatttc agcttcgatt gggatattga tccgagcctg    1020
attatcaaag tttggagcaa aaatgaagaa agcatgtatg aaaccggcac catcgttgat    1080
ctgccgaatg tcgtcgtta tattgatctg gttgcaagct ataatgaaag caataccctg    1140
cagctgaaaa aagaggttac ctggaaaccg atgttctatc atgttattca tccgaccccg    1200
agcgttccgg cactggttaa agcaaaagcc ggtgcaggta atctgcat                 1248
```

<210> SEQ ID NO 8
<211> LENGTH: 1248
<212> TYPE: DNA
<213> ORGANISM: Bacillus spec.

<400> SEQUENCE: 8

```
aaagaactgg gtcatgatgt gctgaaaccg tatgatggtt gggcaagcta tggtgaaggt       60
acaaccggtg gtagcatggc aagtccgcag aatgtttata ccgttaccaa taaaaccgaa      120
ctggttcagg cactgggtgg taataatcat accaatcagt ataattccgt gccgaaaatc      180
atctatgtga aaggcaccat tgaactgaac gtggatgata ataatcagcc ggttggtccg      240
gaattctata aagatccgca ttatgatttt gaagcctatc tgaaagagta tgatccgaaa      300
aaatggggca aaaagaagt tagcggtccg ctggaagaag cacgcgcacg tagccagaaa       360
aaacagaaag aacgtattgt tgtgaatgtg ggtagcaaca ccagcattat tggtgttggt      420
aaagatgcca aaattgtggg tggtggtttc ctgattaaaa acgtggataa tgtgatcatc      480
cgcaacatcg aatttgaagc accggtggat tattttccgg aatgggatcc gaccgatggc      540
accctgggtg aatggaatag cgaatatgat agcattacca ttgaaggcag ccatcatatt      600
tggatcgatc acaataccct taccgatggc gatcatccgg ataaaagcct gggcaccctat     660 tttggtcgtc cgtttcagca gcatgatggc gcactggata tcaaaaatag cagcgatttt     720
atcaccatca gctacaacgt gtttaaagac catgataaag tgaccctgat tggtgcaagc    780
gatagccgta tggcagatga aggtcatctg cgtgttaccc tgcatcacaa ttattacaaa     840
aatgttaccc agcgtctgcc tcgtgttcgt tttggtcagg ttcatatcta taacaactac     900
tatgagttta gcaacctggc cgattatgac tttcagtatg catggggtgt tggtgttgaa    960
agcaaaatct atgcccagaa caactatttc agcttcgatt gggatattga cccgagcaaa    1020
```

```
attatcaaag tttggagcaa aaacgaagaa agcatgtatg aaagcggtac gattgttgat    1080
ctgccgaatg tcgtcgtta tattgatctg gttgcaagct ataatgaaag caataccctg    1140
cagctgaaaa aagaggttgg ttggaaaccg atgttctatc atgttattca tccgaccccg    1200
agcgttccgg cactggttaa agcaaaagcc ggtgcaggta atctgcat                1248
```

<210> SEQ ID NO 9
<211> LENGTH: 1248
<212> TYPE: DNA
<213> ORGANISM: Bacillus spec.

<400> SEQUENCE: 9

```
aaagaactgg gtcatgatgt gctgaaaccg aatgatggtt gggcaagcta tggtgaaggt     60
acaaccggtg gtagcgaagc aagtccggat aatgtttata ccgttaccaa taaaagcgaa    120
ctggttcagg cactgggtgg taataatcat accaatcagt ataattccac cccgaaaatc    180
atctatgtga aaggcaccat tgaactgaac gtggatgata taatcagcc ggttggtccg     240 gaatattatg atgatccgca ttatgatttt gaagcctatc tgaaagagta tgatccgaaa    300
aaatggggca aaaagaagt tagcggtccg ctggaagaag cacgcgcacg tagccagaaa    360
aaacagaaag aacgtattgt tgtgaatgtg ggtagcaaca ccagcattat tggtgttggt    420
aaagatgcca aaattgtggg tggtggtttc ctgattaaaa acgtggataa tgtgatcatc    480
cgcaacatcg aatttgaagc accggttgat tttttccggg aatgggatcc gaccgatggt    540
gaatatggcg aatggaatag cgaatatgat agcattacca tcgaaagcag ccatcatatt    600
tggatcgatc acaatacctt taccgatggc gatcatccgg ataaaagcct gggcacctat    660
tttggtcgtc cgtttcagca gcatgatggc gcactggata tcaaaaatag cagcgatttt    720
atcaccatca gctacaacgt gtttaaagac catgataaag tgagcctgat tggttcaagc    780
gatagccgta aaccgatga aggtcatctg aaagttaccc tgcatcacaa ctattacaaa    840
aatgttaccc agcgtctgcc tcgtgttcgt tttggtcagg ttcatatcta taacaactac    900
tatgagttta gcaacctggc cgattatgac tttcagtatg catgggtgt tggtgttgaa    960 agcaaaatct atgcccagaa caactatttc agcttcgatt gggatattga cccgagcaaa    1020
attatcaaag tttggagcaa aaacgaagaa agcatgtatg aaagcggtac gattgttgat    1080
ctgccgaatg tcgtcgtta tattgatctg gttgcaagct ataatgaaag caataccctg    1140
cagctgaaaa aagaggttgg ttggaaaccg atgttctatc atgttattca tccgaccccg    1200
agcgttccgg cactggttaa agcaaaagcc ggtgcaggta atctgcat                1248
```

<210> SEQ ID NO 10
<211> LENGTH: 1248
<212> TYPE: DNA
<213> ORGANISM: Bacillus spec.

<400> SEQUENCE: 10

```
aaagaactgg gtcatgaagt tctgaaaccg tatgatggtt gggcagcgta tggtgaaggt     60
acaaccggtg gtgcaatggc aagtccgcag aatgtttttg ttgttaccaa tcgtaccgaa    120
ctgattcagg cactgggtgg taataatcat accaatcagt ataattccgt gccgaaaatc    180
atctatgtga aaggcaccat tgatctgaac gtggatgata taatcagcc ggttggtccg    240 gatttctata agatccgca ttttgatttt gaggcctatc tgcgtgaata tgatccggca    300
acctggggta aaaagaagt tgaaggtccg ctggaagaag cacgcgttcg tagccagaaa    360
aaacagaaag atcgtatcat ggtttatgtg ggtagcaaca ccagcattat tggtgttggt    420
```

```
aaagacgcga aaatcaaagg tggtggtttc ctgattaaaa acgtggataa tgtgatcatc    480
cgcaacatcg aatttgaagc accgctggat tattttccgg aatgggatcc gaccgatggc    540
accctgggtg aatggaatag cgaatatgat agcattagca ttgaaggcag cagccatatt    600
tggattgatc acaatacctt taccgatggc gatcatccgg atcgtagcct gggcaccctat 660 tttggtcgtc cgtttcagca gcatgatggc ctgctggata tcaaaaatag cagcgatttt    720
atcaccatca gctacaacgt gtttaccaac cacgataaag ttaccctgat tggtgcaagc    780
gatagccgta tggcagatag cggtcatctg cgtgttaccc tgcatcacaa ttattacaaa    840
aatgttaccc agcgtctgcc tcgtgttcgt tttggtcagg ttcatatcta taacaactac    900
tatgagttta gcaacctggc cgattatgat tttcagtatg catggggtgt tggtgtgttt    960
agccagattt atgcacagaa caactatttc agcttcgatt gggatattga tccgagcctg   1020
attatcaaag tttggagcaa aaatgaagaa agcatgtatg aaaccggcac catcgttgat   1080
ctgccgaatg tcgtcgtta tattgatctg gttgcaagct ataatgaaag caatacctg    1140 cagctgaaaa aagaggttac ctggaaaccg atgttctatc atgttattca tccgaccccg   1200
agcgttccgg cactggttaa agcaaaagcc ggtgcaggta atctgcat               1248

<210> SEQ ID NO 11
<211> LENGTH: 1248
<212> TYPE: DNA
<213> ORGANISM: Bacillus spec.

<400> SEQUENCE: 11
aaagaactgg gtcatgatgt gctgaaaccg tatgatggtt gggcaagcta tggtgaaggt     60
acaaccggtg gtagcatggc aagtccgcag aatgtttata ccgttaccaa taaaaccgaa    120
ctggttcagg cactgggtgg taataatcat accaatcagt ataattccgt gccgaaaatc    180
atctatgtga aaggcaccat tgaactgaac gtggatgata taatcagcc ggttggtccg     240 gaattctata agatccgca ttatgatttt gaagcctatc tgaaagagta tgatccgaaa    300
aaatggggca aaaagaagt tagccggtccg ctggaagaag cacgcgcacg tagccagaaa    360
aaacagaaag aacgtattgt tgtgaatgtg ggtagcaaca ccagcattat tggtgttggt    420
aaagatgcca aaattgtggg tggtggtttc ctgattaaaa acgtggataa tgtgatcatc    480
cgcaacatcg aatttgaagc accggtggat tattttccgg aatgggatcc gaccgatggc    540
accctgggtg aatggaatag cgaatatgat agcattacca ttgaaggcag ccatcatatt    600
tggatcgatc acaataccttt taccgatggc gatcatccgg ataaaagcct gggcaccctat 660 tttggtcgtc cgtttcagca gcatgatggc ctgctggata tcaaaaatag cagcgatttt    720
atcaccatca gctacaacgt gtttaaagac catgataaag tgaccctgat tggtgcaagc    780
gatagccgta tggcagatga aggtcatctg cgtgttaccc tgcatcacaa ttattacaaa    840
aatgttaccc agcgtctgcc tcgtgttcgt tttggtcagg ttcatatcta taacaactac    900
tatgagttta gcaacctggc cgattatgac tttcagtatg catggggtgt tggtgttgaa    960
agcaaaatct atgcccagaa caactatttc agcttcgatt gggatattga cccgagcaaa   1020
attatcaaag tttggagcaa aaacgaagaa agcatgtatg aaagcggtac gattgttgat   1080
ctgccgaatg tcgtcgtta tattgatctg gttgcaagct ataatgaaag caatacctg    1140 cagctgaaaa aagaggttgg ttggaaaccg atgttctatc atgttattca tccgaccccg   1200
agcgttccgg cactggttaa agcaaaagcc ggtgcaggta atctgcat               1248
```

<210> SEQ ID NO 12
<211> LENGTH: 1248
<212> TYPE: DNA
<213> ORGANISM: Bacillus spec.

<400> SEQUENCE: 12

| | | | | | |
|---|---|---|---|---|---|
| aaagaactgg | gtcatgatgt | gctgaaaccg | aatgatggtt | gggcaagcta | tggtgaaggt | 60 |
| acaaccggtg | gtagcgaagc | aagtccggat | aatgtttata | ccgttaccaa | taaaagcgaa | 120 |
| ctggttcagg | cactgggtgg | taataatcat | accaatcagt | ataattccac | cccgaaaatc | 180 |
| atctatgtga | aaggcaccat | tgaactgaac | gtggatgata | taatcagcc | ggttggtccg | 240 |
| gaatattatg | atgatccgca | ttatgatttt | gaagcctatc | tgaaagagta | tgatccgaaa | 300 |
| aaatggggca | aaaagaagt | tagcggtccg | ctggaagaag | cacgcgcacg | tagccagaaa | 360 |
| aaacagaaag | aacgtattgt | tgtgaatgtg | ggtagcaaca | ccagcattat | tggtgttggt | 420 |
| aaagatgcca | aaattgtggg | tggtggtttc | ctgattaaaa | acgtggataa | tgtgatcatc | 480 |
| cgcaacatcg | aatttgaagc | accggttgat | ttttttccgg | aatgggatcc | gaccgatggt | 540 |
| gaatatggcg | aatggaatag | cgaatatgat | agcattacca | tcgaaagcag | ccatcatatt | 600 |
| tggatcgatc | acaataccct | taccgatggc | gatcatccgg | ataaaagcct | gggcaccctat | 660 |
| tttggtcgtc | cgtttcagca | gcatgatggc | ctgctggata | tcaaaaatag | cagcgatttt | 720 |
| atcaccatca | gctacaacgt | gtttaaagac | catgataaag | tgagcctgat | tggttcaagc | 780 |
| gatagccgta | aaaccgatga | aggtcatctg | aaagttaccc | tgcatcacaa | ctattacaaa | 840 |
| aatgttaccc | agcgtctgcc | tcgtgttcgt | tttggtcagg | ttcatatcta | taacaactac | 900 |
| tatgagttta | gcaacctggc | cgattatgac | tttcagtatg | catggggtgt | tggtgttgaa | 960 |
| agcaaaatct | atgcccagaa | caactatttc | agcttcgatt | gggatattga | cccgagcaaa | 1020 |
| attatcaaag | tttggagcaa | aaacgaagaa | agcatgtatg | aaagcggtac | gattgttgat | 1080 |
| ctgccgaatg | gtcgtcgtta | tattgatctg | gttgcaagct | ataatgaaag | caatacccctg | 1140 |
| cagctgaaaa | aagaggttgg | ttggaaaccg | atgttctatc | atgttattca | tccgaccccg | 1200 |
| agcgttccgg | cactggttaa | agcaaaagcc | ggtgcaggta | atctgcat | | 1248 |

<210> SEQ ID NO 13
<211> LENGTH: 24
<212> TYPE: DNA
<213> ORGANISM: Bacillus Spec

<400> SEQUENCE: 13
gaaattaata cgactcacta tagg                                              24

<210> SEQ ID NO 14
<211> LENGTH: 37
<212> TYPE: DNA
<213> ORGANISM: Bacillus Spec

<400> SEQUENCE: 14
gccatcatgc tgctgaaacg gacgaccaaa ataggtg                                37

<210> SEQ ID NO 15
<211> LENGTH: 39
<212> TYPE: DNA
<213> ORGANISM: Bacillus Spec

<400> SEQUENCE: 15
ggtcgtccgt ttcagcagca tgatggcctg ctggatatc                              39

```
<210> SEQ ID NO 16
<211> LENGTH: 27
<212> TYPE: DNA
<213> ORGANISM: Bacillus Spec

<400> SEQUENCE: 16
ggttatgcta gttattgctc agcggtg                                        27
```